US007683236B2

(12) United States Patent
Boiani et al.

(10) Patent No.: US 7,683,236 B2
(45) Date of Patent: Mar. 23, 2010

(54) ENHANCED PRODUCTION OF CLONED MAMMALS BY ZONA PELLUCIDA-FREE HOMOLOGOUS MAMMALIAN EMBRYO AGGREGATION

(75) Inventors: Michele Boiani, Münster (DE); Kenneth John McLaughlin, Landenberg, PA (US); Hans R. Scholer, Münster (DE)

(73) Assignee: Trustees of the University of Pennsylvania, Philadelphia, PA (US)

( * ) Notice: Subject to any disclaimer, the term of this patent is extended or adjusted under 35 U.S.C. 154(b) by 447 days.

(21) Appl. No.: 10/865,369

(22) Filed: Jun. 10, 2004

(65) Prior Publication Data

US 2005/0005318 A1    Jan. 6, 2005

Related U.S. Application Data

(60) Provisional application No. 60/477,250, filed on Jun. 10, 2003.

(51) Int. Cl.
*C12N 15/00* (2006.01)
*A01K 67/027* (2006.01)

(52) U.S. Cl. ............................ 800/24; 800/15; 800/16; 800/17; 800/18

(58) Field of Classification Search .................. 800/24, 800/8, 13, 15, 18
See application file for complete search history.

(56) References Cited

U.S. PATENT DOCUMENTS

| 2002/0001842 A1 | 1/2002 | Chapman |
| 2003/0087431 A1 | 5/2003 | Alikani et al. |
| 2004/0123337 A1 | 6/2004 | Gleicher |
| 2004/0268422 A1 | 12/2004 | Schatten |

FOREIGN PATENT DOCUMENTS

| WO | WO 2004/091288 | 10/2004 |
| WO | WO 2004/111195 | 12/2004 |

OTHER PUBLICATIONS

Cibelli et al. Cloned Transgenic Calves Produced from Nonquiescent Fetal Fibroblasts. Science. May 22, 1998, vol. 280, pp. 1256-1258.*
Garbutt et al. The Establishment of the Embryonic-Abembryonic Axis in the Mouse Embryo. Development. 1987, vol. 100, pp. 125-134.*
Simerly et al. Molecular Correlates of Primate Nuclear Transfer Failures. Science. Apr. 11, 2003, vol. 300, pp. 297.*
Mitalipov et al. Rhesus Monkey Embryos Produced by Nuclear Transfer from Embryonic Blastomeres or Somatic Cells. Biol. Reproduction. 2002, vol. 66, pp. 1367-1373.*
Boediono et al. Development in vitro and in vivo of Aggregrated Parthenogenetic Bovine Embryos. Reproduct. Fertil. Devel. 1995, vol. 7, pp. 1073-1079.*
Vajta, G., et al., "New Method for Culture of Zona-Included or Zona-Free Embryos: The Well of the Well (WOW) System," Molecular Reproduction and Development, 55:256-264 (2000).
Otaegui, P.J., et al., "Transfer of Nuclei From 8-Cell Stage Mouse Embryos Following Use of Nocodazole to Control the Cell Cycle," Molecular Reproduction and Development, 39:147-152, (1994).
Boediono, A., et al., "Offspring Born From Chimeras Reconstructed From Parthenogenetic and In Vitro Fertilized Bovine Embryos," Molecular Reproduction and Development, 53:159-170, (1999).
Burnside, A.S., et al., "Conduction of Oct-3/4 expression in somatic cells by gap junction-mediated cAMP singaling from blastomeres," European Journal of Cell Biology, 81:585-591, (2002).
Cox, D.R., et al., "Mouse Trisomy 16 as an Animal Model of Human Trisomy 21 (Down Syndrome): Production of Viable Trisomy 16↔Diploid Mouse Chimeras," Developmental Biology, 101:416-424 (1984).
McLaren, A., "Transfer of Zona-Free Mouse Eggs to Uterine Foster Mothers," Journal of Reproductive Fertility, 19:341-346, (1969).
Sekirina, G.G., et al., "The microenvironment created by non-blocking embryos in aggregates may rescue blocking embryos via cell-embryo adherent contacts," Zygote, 3:313-324, (1995).
Alikani, M. and S.M. Willadsen, "Human blastocysts from aggregated mononucleated cells of two or more non-viable zygote-derived embryos," Reprod Biomed Online, 5(1): p. 56-8, (2002).
Suzuki, H., et al., "Developmental ability of zona-free mouse embryos is influenced by cell association at the 4-cell stage," Biol Reprod, 53(1): p. 78-83, (1995).
Yin, X.J., et al., "Production of cloned pigs from adult somatic cells by chemically assisted removal of maternal chromosomes," Biol Reprod, 67(2): p. 442-6, (2002).
Yabuuchi, A., Y. Kato, and Y. Tsunoda, "Effects of aggregation of nuclear-transferred mouse embryos developed from enucleated eggs receiving ES cells on in vitro and in vivo development," Journal of Reproduction and Development, 48(4): p. 393-397, (2002).
Epstein, C.J., et al., "Production of viable adult trisomy 17 reversible diploid mouse chimeras," Proc Natl Acad Sci U S A, 79(14): p. 4376-80, (1982).
Ibanez, E., D.F. Albertini, and E.W. Overstrom, "Demecolcine-induced oocyte enucleation for somatic cell cloning: coordination between cell-cycle egress, kinetics of cortical cytoskeletal interactions, and second polar body extrusion," Biol Reprod, 68(4): p. 1249-58, (2003).
Vance, M.M. and L.M. Wiley, "Gap junction intercellular communication mediates the competitive cell proliferation disadvantage of irradiated mouse preimplantation embryos in aggregation chimeras," Radiat Res, 152(5): p. 544-51, (1999).
Naito, K., Y. Toyoda, and R. Yanagimachi, "Production of normal mice from oocytes fertilized and developed without zonae pellucidae," Hum Reprod, 7(2): p. 281-5, (1992).
Wells, K.D. and A.M. Powell, "Blastomeres from somatic cell nuclear transfer embryos are not allocated randomly in chimeric blastocysts," Cloning, 2(1): p. 9-22, (2000).
Kawakami, M., et al., "Effect of demecolcine and nocodazole on the efficiency of chemically assisted removal of chromosomes and the developmental potential of nuclear transferred porcine oocytes," Cloning and Stem Cells, 5(4): p. 379-87, (2003).

(Continued)

*Primary Examiner*—Deborah Crouch
(74) *Attorney, Agent, or Firm*—Dann, Dorfman, Herrell & Skillman; Robert C. Netter, Jr.

(57) ABSTRACT

Compositions and methods are provided for the efficient and reproducible generation of clone animals of all developmental stages. Also provided are methods of use of the same in reproductive and therapeutic cloning protocols.

28 Claims, 6 Drawing Sheets

OTHER PUBLICATIONS

Sekirina, G.G., et al., "Overcoming the '2-cell block' in mouse embryos in aggregation chimeras," Ontogenez, 27:361-70, (1996), [Abstract].

Tanaka, H., et al., "Influence of Time After the Removal of Nocodazole From Nuclear Donors on the Development of Reconstituted Embryos in Bovine Nuclear Transplantation," Japanese Journal of Veterinary Research, 43:135-143, (1995).

Kwon, O.Y., et al., "Production of identical sextuplet mice by transferring metaphase nuclei from four-cell embryos," Proc. Natl. Acad. Sci. U.S.A., 93: 13010-13013, (1996).

Yang, X., et al., "Potential of Hypertonic Medium Treatment for Embryo Micromanipulation: II. Assessment of Nuclear Transplantation Methodology, Isolation, Subzona Insertion, and Electrofusion of Blastomeres to Intact or Functionally Enucleated Oocytes in Rabbits," Molecular Reproduction and Development, 27:118-129, (1990).

Oback, B., et al., "Cloned Cattle Derived from a Novel Zona-Free Embryo Reconstruction System," Cloning and Stem Cells, 5:3-12, (2003).

Johnson, M.H., et al., "Acid Tyrode's solution can stimulate parthenogenetic activation of human and mouse oocytes," Fertility and Sterility, 53:266-270, (1990).

Colman, A., et al., "Therapeutic cloning: concepts and practicalities," Tibtech, 18:192-196, (2000).

Stewart, C.L., "Oct-4, Scene 1: the drama of mouse development," Nature Genetics, 24:328-330, (2000).

Yoshimizu, T., et al., "Germline-specific expression of the Oct-4/green fluorescent protein (GFP) transgene in mice," Develop. Growth Differ., 41:675-684, (1999).

Kono, T., et al., "Development of enucleated mouse oocytes reconstituted with embryonic nuclei," Journal of Reproductive Fertility, 93:165-172, (1991).

Kono, T., et al., "Development of Androgenetic Mouse Embryos Produced by In Vitro Fertilization of Enucleated Oocytes," Molecular Reproduction and Development, 34:43-46, (1993).

Stevens, L.C., "Totipotent cells of parthenogenetic origin in a chimaeric mouse," Nature, 276:266-267, (1978).

* cited by examiner

ENHANCED PRODUCTION OF CLONED MAMMALS BY ZONA PELLUCIDA-FREE HOMOLOGOUS MAMMALIAN EMBRYO AGGREGATION

The present application claims priority to U.S. Provisional Application 60/477,250 filed Jun. 10, 2003, the entire disclosure of which is incorporated by reference herein.

FIELD OF THE INVENTION

The present invention relates to the fields of embryology and molecular biology. Specifically, methods for the efficient and reproducible generation of clone animal embryos are disclosed. Methods are also provided for the use of the clone animal embryos in reproductive and therapeutic cloning.

BACKGROUND OF THE INVENTION

Several publications and patent documents are cited throughout the specification in order to describe the state of the art to which this invention pertains. Each of these references is incorporated herein as though set forth in full.

Direct somatic cell nuclear injection into a recipient "enucleated" oocyte, which is subsequently cultured under conditions conducive to the formation of blastocysts to be transplanted into a surrogate mother, allows for the production of individuals genetically identical to the donor of the cell (i.e. clones). The production of these clones provides a means for: i) reproduction of a species that cannot reproduce effectively on its own (e.g. endangered species); ii) the production of animals with certain desirable or commercially valuable characteristics (e.g. better performance of dairy farm species); iii) deriving individual specific stem cells from the blastocyst (e.g. therapeutic cloning); and iv) treating infertility given the ability to turn embryonic stem cells into germ cells and ultimately mature eggs (Hubner, K. et al. (2003) Science). Additionally, the nucleus donor cells may be manipulated prior to nuclear transfer, so as to add, subtract, or amend any characteristic that will then be incorporated into the germline of the cloned animal and be transmitted to subsequent generations.

The currently employed methods for cloning animals are very inefficient and often fail to provide reproducible results. The two main procedures used for cloning mammals are the Roslin method and the Honolulu method. These procedures were named after the generation of Dolly the sheep at the Roslin Institute in Scotland in 1996 (Campbell, K. H. et al. (1996) Nature 380:64-66) and of Cumulina the mouse at the University of Hawaii in Honolulu in 1998 (Wakayama, T. et al. (1998) Nature 394:369-374). In contrast to the cloning of farm species based on the Roslin method, the technique used in the cloning of mice by the Honolulu method has remained elusive.

The ability to clone laboratory animals, such as mice, is highly desirable for several reasons. Clones can provide material for therapeutic cloning. The ability to produce embryonic stem (ES) cells has only been established in mice and humans. The mouse is the only species where an example of therapeutic cloning has been accomplished and where ES cells have been differentiated into mature oocytes, though the employed techniques may be employable in other species including humans (Rideout, W. M. et al. (2002) Cell 109:17-27; Hubner, K. et al. (2003) Science). Moreover, the handling and costs associated with a mouse model are practical and the genome is well studied. Additionally, the gestation period of the mouse is only 3 weeks as compared to 9 and 4 months for bovine and ovine species, respectively.

Cloned animals have exhibited a similar set of defects regardless of species. Specifically, dysregulation of gene expression during embryogenesis, placentomegaly during gestation, respiratory failure at birth, and conditions in the adult such as obesity, immunodeficiency and seizure are common. No corrective procedures to eliminate such defects have yet been developed that do not involve the passage through the germline (Tamashiro, K. L. et al. (2002) Nat. Med. 8:262-267) or the derivation of ES cells (Rideout, W. M. et al. supra). While these interventions can benefit the next generation or the adult, they are completely ineffective for correcting defects during prenatal stages. It is at the prenatal stages, however, where the greatest amount of attrition in clones occurs. Additionally, current procedures seldom result in the delivery of more than one clone per gestation in those species where this is naturally the case (e.g. mouse, pig) and call for extraordinary perinatal care. Therefore, improved methods which minimize this attrition during the prenatal stages would be most advantageous.

All of the defects cited above are related, directly or indirectly, to alterations that occur in the expression of the genetic material of the donor nucleus upon transplantation into the oocyte. There is a consensus that "reprogramming" of the donor genetic material begins soon after transplantation, but this "reprogrammed" nucleus is seldom equivalent to the state of a zygotic nucleus (i.e. reprogramming is either incomplete or faulty). Indeed, an analysis of global gene expression by cDNA microarray technology shows that the expression of a number of genes is consistently biased due to the general cloning procedure employed while other genes are abnormally expressed in relation to the type of donor nucleus (Humpherys, D. et al. (2002) Proc. Natl. Acad. Sci. 99:12889-12894). The level of reprogramming obtained likely relates to the subsequent phenotype of the clone animal. It is unclear, however, to what extent gene expression defects at early stages practically contribute to subsequent postimplantation impairment or demise of clones. A viable approach to gene expression analysis (e.g. a GFP-tagged transgene reporter) may allow the determination of the effects of certain gene expression defects (Boiani, M. et al. (2002) Genes Dev. 6:1209-1219).

The expression of the POU-domain transcription factor Oct4, which is expressed in pluripotent cells and is evolutionarily conserved in humans, bovine, and mice (Nordhoff, V. et al. (2001) Mamm. Genome 12:309-317), is required at the morula stage to prepare for the first cell lineage decision (Nichols, J. et al. (1998) Cell 95:379-391). In normal blastocysts, Oct4 expression is maintained only in the inner cell mass and downregulated in the trophectoderm. It has been previously demonstrated that the distribution and level of Oct4 is abnormal in 2 out of every 3 somatic cell derived mouse clones at the blastocyst stage and this ratio correlates well with the inability to form ES cells (Boiani, M. et al. (2002) Genes Dev. 6:1209-1219). Notably, gap junction mediated signaling has been shown to induce Oct4 expression in epithelial-like cells placed in contact with embryo blastomeres (Burnside, A. S. and P. Collas (2002) Eur. J. Cell. Biol. 81:585-591). This indicates that alternative routes for reprogramming may exist in addition to or in association with the direct exposure of a donor nucleus to the ooplasm.

Typically, much less than 50% of clone mouse embryos produced by current techniques attain a level of reprogramming compatible with blastocyst formation. Additionally, less than 5% of clone mouse embryos attain a level of reprogramming compatible with postimplantation development and birth. It is therefore highly desirable that improved methods be developed to increase viable mouse clone yields.

SUMMARY OF THE INVENTION

In accordance with the present invention, a method for enucleating a cell, in particular an oocyte, is provided. Specifically, the cell is incubated with microtubule inhibitors which disrupt the mitotic or meiotic spindle (e.g. nocodazole) and actin depolymerizing agents (e.g. cytochalasin B). Following such treatment, the chromosomes are subsequently removed by micromanipulation.

In another embodiment of the invention, a method for preparing a non-human blastocyst capable of developing into a live-born animal is provided. An exemplary method comprises the steps of: a) providing a reconstructed, embryos; b) removing the zona pellucida of the embryos; c) aggregating at least two zona-free embryos, typically at the 4-cell stage; and d) culturing the embryo aggregate of c) under conditions which result in the formation of a blastocyst. Optionally, the method further comprises implanting the obtained blastocyst into a recipient female so as to produce a fetus that undergoes full fetal development and parturition to generate a live born animal. Additionally, the donor cell may be transformed with a heterologous nucleic acid sequence prior to transferring the nucleus of the donor cell into an enucleated oocyte. Aggregated embryos having increased biomass and excess extranuclear cytoplasmic factors (e.g., cAMP) or other growth factors such as acrogranin are also encompassed within the invention. These factors facilitate gene expression, blastocyst formation and enhanced viability. In one embodiment, such embryos may be prepared by the method described above.

In yet another aspect of the instant invention, a method for the therapeutic cloning of tissues for the treatment of disease in a patient is provided. Specifically, the method comprises the steps of: a) providing reconstructed embryos; b) removing the zona pellucida of the embryos; c) aggregating at least two zona-free embryos, typically at the 4-cell stage; d) culturing the aggregate of zona-free embryos from step c) under conditions suitable to induce blastocyst formation; and e) isolating embryonic stem cells from the blastocyst. Stem cells so isolated have a number of different utilities. The method may further comprise exposing the isolated cells to a receptor ligand cocktail which induces the stem cells to differentiate into a desired cell type; culturing the cells for a suitable time period to generate an effective amount of cells of the desired cell type; and optionally isolating the cells for use in therapeutic protocols. Optionally, the donor cells, prior to transferring the nucleus of the donor cell into the enucleated oocyte, and the isolated stem cells may be transformed with a heterologous nucleic acid sequence.

In yet another embodiment of the invention, another method for therapeutic cloning of tissues for the treatment of disease in a patient is provided. Specifically, the method comprises the steps of: a) providing reconstructed embryos; b) removing the zona pellucida of the embryos; c) aggregating at least two zona-free embryos, typically at the 4-cell stage; d) culturing the aggregate of zona-free embryos from step c) under conditions suitable to induce blastocyst formation; e) isolating embryonic stem cells from the formed blastocyst; f) transforming the isolated stem cells with a nucleic acid construct encoding a tissue specific molecule operably linked to a sequence encoding a selectable marker; g) culturing the cells in the presence of the selection agent thus allowing only those cells expressing the construct to survive and generating a culture of the desired cell type; h) culturing the cells of step g) for a suitable time period to generate an effective amount of cells of the desired cell type; and i) optionally isolating the cells of step h). Optionally, the somatic cells, prior to transferring the nucleus of the somatic cell into the enucleated oocyte, and the isolated stem cells may be transformed with a corrective nucleic acid sequence.

BRIEF DESCRIPTIONS OF THE DRAWING

Figure 5:
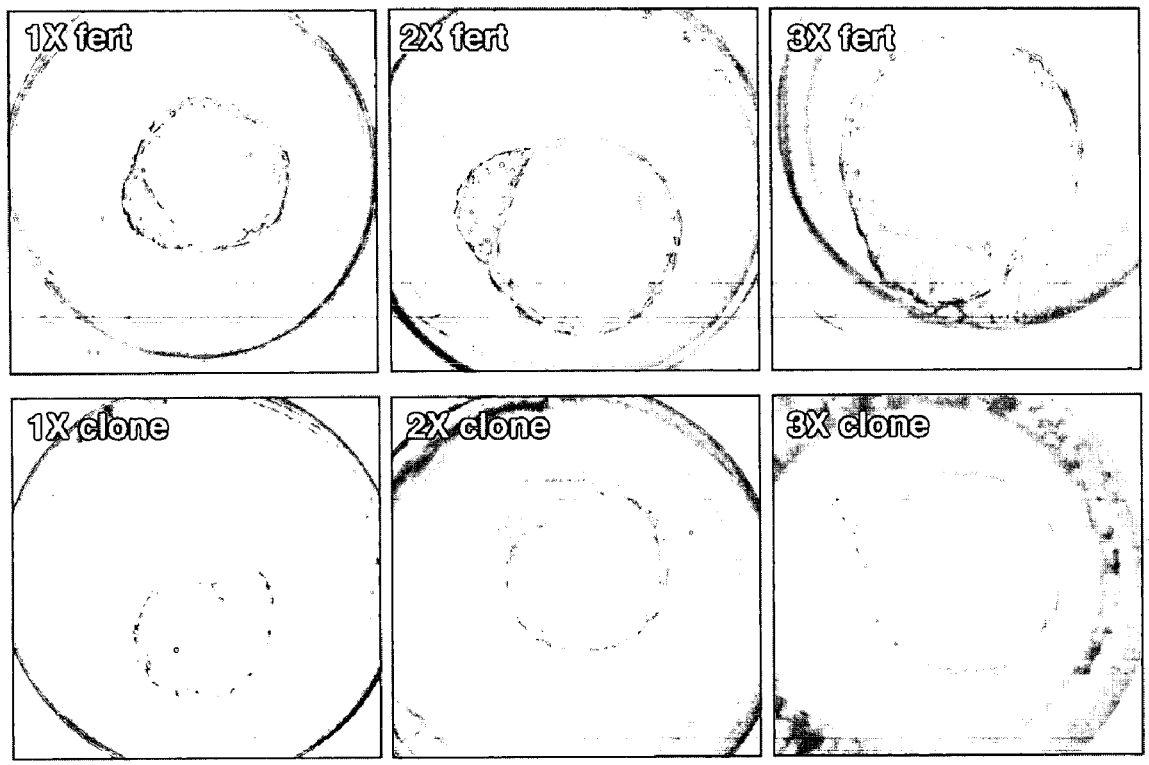

FIG. 5 is a series of images comparing clone blastocysts of the instant invention from a single 4-cell embryo (1X), an aggregation of two 4-cell clone embryos (2X), and an aggregation of three 4-cell clone embryos (3x) in comparison to fertilized controls (top 3 panels).

Figure 6:
Figure 6:

FIG. 6 contains photographs of clone pups obtained from a single pregnancy following the method of the instant invention. Note the four pups in one gestation in the right panel.

DETAILED DESCRIPTION OF THE INVENTION

In accordance with the present invention, compositions and methods for the efficient and reproducible generation of clone animal embryos are provided (referred to herein as the University of Pennsylvania method).

The following definitions are provided to facilitate an understanding of the present invention:

The term "autologous" implies total nuclear genetic identity between donor cells or tissue and those of the recipient.

A "hybrid cell" refers to the cell immediately formed by the fusion of a unit of cytoplasm formed from the fragmentation of an oocyte or zygote with an intact somatic or stem cell or alternatively a derivative portion of said somatic or stem cell, containing the nucleus.

The term "karyoplast" refers to a fragment of a cell containing the chromosomes and nuclear DNA. A karyoplast is surrounded by a membrane, either the nuclear membrane or other natural or artificial membrane.

"Multipotent" implies that a cell is capable, through its progeny, of giving rise to several different cell types found in the adult animal.

"Pluripotent" implies that a cell is capable, through its progeny, of giving rise to all the cell types which comprise the adult animal including the germ cells. Both embryonic stem and embryonic germ cells are pluripotent cells under this definition.

A "reconstructed embryo" is an embryo made by the fusion of an enucleated oocyte with a donor somatic or embryonic stem (ES) or embryonic germ (EG) cell; alternatively, the donor cell nucleus can be isolated and injected into the oocyte. In yet another approach chromatin or nuclear DNA may be injected into the oocyte to create the reconstructed embryo.

The term "transgenic" animal or cell refers to animals or cells whose genome has been subject to technical intervention including the addition, removal, or modification of genetic information. The term "chimeric" refers an entity such as an individual, organ, cell, nucleic acid or part thereof consisting of regions derived from entities of diverse genetic constitution.

A "zygote" refers to a fertilized one-cell embryo.

The term "totipotent" as used herein can refer to a cell that gives rise to a live born animal. The term "totipotent" can also refer to a cell that gives rise to all of the cells in a particular animal. A totipotent cell can give rise to all of the cells of an animal when it is utilized in a procedure for developing an embryo from one or more nuclear transfer steps. Totipotent cells may also be used to generate incomplete animals such as those useful for organ harvesting, e.g., having genetic modifications to eliminate growth of an organ or appendage by manipulation of a homeotic gene. Additionally, genetic modification rendering oocytes, such as those derived from ES cells, incapable of development in utero would ensure that human derived ES cells could not be used to derive human oocytes for reproduction and only for applications such as therapeutic cloning.

A "blastocyst" is a preimplantation embryo that develops from a morula. A blastocyst has an outer layer called the trophoblast that is required for implantation into the uterine epithelium and an inner cell mass that contains the embryonic stem cells and will give rise to the embryo proper. A blastocyst normally contains a blastocoel or a blastocoelic cavity.

The term "follicle" refers to a more or less spherical mass of cells sometimes forming a cavity. Ovarian follicles comprise egg cells and the corona radiata.

An "embryoid body" (EB) is a three dimensional structure that forms from differentiated embryonic stem cells. Cellular derivatives of all three germ layers have been generated from embryoid bodies, such as hematopoietic, endothelial, muscle and neuronal cells.

The term "live born" as used herein preferably refers to an animal that exists ex utero. A "live born" animal may be an animal that is alive for at least one second from the time it exits the maternal host. A "live born" animal may not require the circulatory system of an in utero environment for survival. A "live born" animal may be an ambulatory animal. Such animals can include pre- and post-pubertal animals. As discussed previously, a live born animal may lack a portion of what exists in a normal or wild-type animal of its kind.

The term "cultured" as used herein in reference to cells can refer to one or more cells that are undergoing cell division or not undergoing cell division in an in vitro environment. An in vitro environment can be any medium known in the art that is suitable for maintaining cells in vitro, such as suitable liquid media or agar, for example. Specific examples of suitable in vitro environments for cell cultures are described in Culture of Animal Cells: a manual of basic techniques (3.sup.rd edition), 1994, R. I. Freshney (ed.), Wiley-Liss, Inc.; Cells: a laboratory manual (vol. 1), 1998, D. L. Spector, R. D. Goldman, L. A. Leinwand (eds.), Cold Spring Harbor Laboratory Press; and Animal Cells: culture and media, 1994, D. C. Darling, S. J. Morgan John Wiley and Sons, Ltd.

The term "cell line" as used herein can refer to cultured cells that can be passaged at least one time without terminating. The invention relates to cell lines that can be passaged at least 1, 2, 5, 10, 15, 20, 30, 40, 50, 60, 80, 100, and 200 times. Cell passaging is defined hereafter.

The term "suspension" as used herein can refer to cell culture conditions in which cells are not attached to a solid support. Cells proliferating in suspension can be stirred while proliferating using apparatus well known to those skilled in the art.

The term "monolayer" as used herein can refer to cells that are attached to a solid support while proliferating in suitable culture conditions. A small portion of cells proliferating in a monolayer under suitable growth conditions may be attached to cells in the monolayer but not to the solid support. Preferably less than 15% of these cells are not attached to the solid support, more preferably less than 10% of these cells are not attached to the solid support, and most preferably less than 5% of these cells are not attached to the solid support.

The term "plated" or "plating" as used herein in reference to cells can refer to establishing cell cultures in vitro. For example, cells can be diluted in cell culture media and then added to a cell culture plate, dish, or flask. Cell culture plates are commonly known to a person of ordinary skill in the art. Cells may be plated at a variety of concentrations and/or cell densities.

The term "cell plating" can also extend to the term "cell passaging." Cells of the invention can be passaged using cell culture techniques well known to those skilled in the art. The term "cell passaging" can refer to a technique that involves the steps of (1) releasing cells from a solid support or substrate and disassociation of these cells, and (2) diluting the cells in media suitable for further cell proliferation. Cell passaging may also refer to removing a portion of liquid medium containing cultured cells and adding liquid medium to the original culture vessel to dilute the cells and allow further cell proliferation. In addition, cells may also be added to a new culture vessel which has been supplemented with medium suitable for further cell proliferation.

The term "proliferation" as used herein in reference to cells can refer to a group of cells that can increase in number over a period of time.

The term "permanent" or "immortalized" as used herein in reference to cells can refer to cells that may undergo cell division and double in cell numbers while cultured in an in vitro environment a multiple number of times until the cells terminate. A permanent cell line may double over 10 times before a significant number of cells terminate in culture. Preferably, a permanent cell line may double over 20 times or over 30 times before a significant number of cells terminate in culture. More preferably, a permanent cell line may double over 40 times or 50 times before a significant number of cells terminate in culture. Most preferably, a permanent cell line may double over 60 times before a significant number of cells die in culture.

The term "alkaline phosphatase (AP) positive" as used herein can refer to a detectable presence of cellular alkaline phosphatase. Alkaline phosphatase is typically highly expressed in certain cells such as, without limitation, pluripotent cells, embryonic germ cells, primordial germ cells, and ES cells. Cells that are not alkaline phosphatase positive do not stain appreciably using a procedure for visualizing cellular alkaline phosphatase. Procedures for detecting the presence of cellular alkaline phosphatase are well-known to a person of ordinary skill in the art. See, e.g., Matsui et al., 1991, "Effect of Steel Factor and Leukemia Inhibitory Factor on Murine Primordial Germ Cells in Culture," Nature 353: 750-752. Examples of cells that stain appreciably for alkaline phosphatase can be found in the art. See, e.g., U.S. Pat. No. 5,453,357, entitled "Pluripotent Embryonic Stem Cells and Methods of Making Same," issued to Hogan on Sep. 26, 1995.

The term "precursor cell" or "precursor cells" as used herein can refer to a cell or cells used to establish cultured mammalian cells or a cultured mammalian cell line. A precursor cell or cells may be isolated from nearly any cellular entity. For example, a precursor cell or cells may be isolated from blastocysts, embryos, fetuses, and cell lines (e.g., cell lines established from embryonic cells), preferably isolated from fetuses and/or cell lines established from fetal cells, and more preferably isolated from ex utero animals and/or cell cultures and/or cell lines established from such ex utero animals. An ex utero animal may exist as a newborn animal (e.g., 5 days after birth), adolescent animal (e.g., pre-pubescent animal), pubescent animal (e.g., after ovulation or production of viable sperm), and adult animal (e.g., post pubescent). The ex utero animals may be alive or post mortem. Precursor cells may be cultured or non-cultured. Furthermore, the term "cryopreserving" as used herein can refer to freezing a cell, embryo, or animal of the invention. Cells, embryos, or portions of animals of the invention are frozen at temperatures preferably lower than 0° C., more preferably lower than −80° C., and most preferably at temperatures lower than −196° C. Cells and embryos of the invention can be cryopreserved for an indefinite amount of time. It is known that biological materials can be cryopreserved for more than fifty years and still remain viable. For example, bovine semen that is cryopreserved for more than fifty years can be utilized to artificially inseminate a female bovine animal and result in the birth of a live offspring. Methods and tools for cryopreservation are well-known to those skilled in the art. See, e.g., U.S. Pat. No. 5,160,312, entitled "Cryopreservation Process for Direct Transfer of Embryos," issued to Voelkel on Nov. 3, 1992.

The term "reprogramming" or "reprogrammed" as used herein may refer to materials and methods that can convert a cell into another cell having at least one differing characteristic. Additionally, "reprogramming" of a nucleus may refer to altering the expression pattern of the genome of the nucleus. Also, such materials and methods may reprogram a nucleus to convert (e.g. differentiate) a cell into another cell type that is not typically expressed during the life cycle of the former cell. For example, (1) a non-totipotent cell can be converted into a totipotent cell; (2) a precursor cell can be converted into a cell having a morphology of an embryonic germ (EG) cell; and (3) a precursor cell can be converted into a totipotent cell.

The phrase "embryonal carcinoma cells" refers to cancer cells that exhibit the properties of multipotent stem cells and have the capacity for differentiation into different cell lineages.

The term "isolated" as used herein can refer to a cell that is mechanically separated from another group of cells. Examples of a group of cells are a developing cell mass, a cell culture, a cell line, and an animal.

The term "non-embryonic cell" as used herein can refer to a cell that is not isolated from an embryo. Non-embryonic cells can be differentiated or nondifferentiated. Non-embryonic cells can refer to nearly any somatic cell, such as cells isolated from an ex utero animal. These examples are not meant to be limiting.

For the purposes of the present invention, the term "embryo" or "embryonic" as used herein can refer to a developing cell mass that has not implanted into the genital tract (e.g. uterus) of a maternal host. Hence, the term "embryo" as used herein can refer to a fertilized oocyte, a pre-blastocyst stage developing cell mass, and/or any other developing cell mass that is at a stage of development prior to implantation into the uterine wall of a maternal host. Embryos of the invention may not display a genital ridge. An "embryonic cell" is isolated from and/or has arisen from an embryo. An embryo can represent multiple stages of cell development. For example, a one cell embryo can be referred to as a zygote, a solid spherical mass of cells resulting from a cleaved embryo can be referred to as a morula, and an embryo having a blastocoel can be referred to as a blastocyst.

The term "fetus" as used herein can refer to a developing cell mass that has implanted into the uterine membrane of a maternal host. A fetus can include such defining features as a genital ridge, for example. A genital ridge is a feature easily identified by a person of ordinary skill in the art, and is a recognizable feature in fetuses of most animal species.

The term "fetal cell" as used herein can refer to any cell isolated from and/or has arisen from a fetus or derived from a fetus, including amniotic cells. The term "non-fetal cell" is a cell that is not derived or isolated from a fetus.

The term "parturition" as used herein can refer to a time that a fetus is delivered from female recipient. A fetus can be delivered from a female recipient by abortion, c-section, or birth.

The term "primordial germ cell" as used herein can refer to a diploid precursor cell capable of becoming a germ cell. Primordial germ cells can be isolated from any tissue in a developing cell mass, and are preferably isolated from genital ridge cells of a developing cell mass. A genital ridge is a section of a developing cell mass that is well-known to a person of ordinary skill in the art.

The term "embryonic stem cell" as used herein can refer to pluripotent cells isolated from an embryo that are maintained in in vitro cell culture. Such cells are rapidly dividing cultured cells isolated from cultured embryos which retain in culture the ability to give rise, in vivo, to all the cell types which comprise the adult animal, including the germ cells. Embryonic stem cells may be cultured with or without feeder cells. Embryonic stem cells can be established from embryonic cells isolated from embryos at any stage of development, including blastocyst stage embryos and pre-blastocyst stage embryos. Embryonic stem cells may have a rounded cell morphology and may grow in rounded cell clumps on feeder layers. Embryonic stem cells are well known to a person of ordinary skill in the art. See, e.g., WO 97/37009, entitled "Cultured Inner Cell Mass Cell-Lines Derived from Ungulate Embryos," Stice and Golueke, published Oct. 9, 1997, and Yang & Anderson, 1992, Theriogenology 38: 315-335. See, e.g., Piedrahita et al. (1998) Biol. Reprod. 58: 1321-1329; Wianny et al. (1997) Biol. Reprod. 57: 756-764; Moore & Piedrahita (1997) In Vitro Cell Biol. Anim. 33: 62-71; Moore, & Piedrahita, (1996) Mol. Reprod. Dev. 45: 139-144; Wheeler (1994) Reprod. Fert. Dev. 6: 563-568; Hochereau-de Reviers & Perreau, Reprod. Nutr. Dev. 33: 475-493; Strojek et al., (1990) Theriogenology 33: 901-903; Piedrahita et al., (1990) Theriogenology 34: 879-901; and Evans et al., (1990) Theriogenology 33: 125-129.

The term "differentiated cell" as used herein can refer to a precursor cell that has developed from an unspecialized phenotype to a specialized phenotype. For example, embryonic cells can differentiate into an epithelial cell lining the intestine. Materials and methods of the invention can reprogram differentiated cells into totipotent cells. Differentiated cells can be isolated from a fetus or a live born animal, for example.

The term "undifferentiated cell" as used herein can refer to a precursor cell that has an unspecialized phenotype and is capable of differentiating. An example of an undifferentiated cell is a stem cell.

The term "asynchronous population" as used herein can refer to cells that are not arrested at any one stage of the cell cycle. Many cells can progress through the cell cycle and do not arrest at any one stage, while some cells can become arrested at one stage of the cell cycle for a period of time.

Some known stages of the cell cycle are G1, S, G2, and M. An asynchronous population of cells is not manipulated to synchronize into any one or predominantly into any one of these phases. For example, cells can be arrested in certain stages of the cell cycle, by utilizing multiple techniques known in the art, such as by colcemid (M stage) exposure or aphidicolin (G1/S stage) exposure. Examples of methods for arresting cells at various stages of the cell cycle are discussed in WO 97/07669, entitled "Quiescent Cell Populations for Nuclear Transfer".

The terms "synchronous population" and "synchronizing" as used herein can refer to a fraction of cells in a population that are within a same stage of the cell cycle. Preferably, about 50% of cells in a population of cells are arrested in one stage of the cell cycle, more preferably about 70% of cells in a population of cells are arrested in one stage of the cell cycle, and most preferably about 90% of cells in a population of cells are arrested in one stage of the cell cycle. Cell cycle stage can be distinguished by relative cell size as well as by a variety of cell markers well known to a person of ordinary skill in the art. For example, cells can be distinguished by such markers by using flow cytometry techniques. Alternatively, cells can be distinguished by techniques which distinguish cells based on cell size, such as by the utilization of a light microscope and a micrometer. In a preferred embodiment, cells are synchronized by arresting them (i.e., cells are not dividing) in a discrete stage of the cell cycle.

The terms "embryonic germ cell" and "EG cell" as used herein can refer to a cultured cell that has a distinct flattened morphology and can grow within monolayers in culture. An EG cell may be distinct from a fibroblast cell. This EG cell morphology is to be contrasted with cells that have a spherical morphology and form multicellular clumps on feeder layers. Embryonic germ cells may not require the presence of feeder layers or presence of growth factors in cell culture conditions. Additionally, germ cells may be derived from stem cells transformed with the Oct4 transgene as described more fully in the examples below.

The term "cumulus cell" as used herein can refer to any cultured or non-cultured cell that is isolated from cells and/or tissue surrounding an oocyte. Persons skilled in the art can readily identify a cumulus cell. Examples of methods for isolating and culturing cumulus cells are discussed in Damiani et al. (1996) Mol. Reprod. Dev. 45: 521-534; Long et al. (1994) J. Reprod. Fert. 102: 361-369; and Wakayama et al. (1998) Nature 394: 369-373.

The term "modified nuclear DNA" as used herein can refer to a nuclear deoxyribonucleic acid sequence of a cell, embryo, fetus, or animal of the invention that has been manipulated by one or more recombinant DNA techniques. Examples of recombinant DNA techniques well known to a person of ordinary skill in the art, can include (1) inserting a DNA sequence from another organism (e.g., a human organism) into target nuclear DNA, (2) deleting one or more DNA sequences from target nuclear DNA, and (3) introducing one or more base mutations (e.g., site-directed mutations) into target nuclear DNA. Cells with modified nuclear DNA can be referred to as "transgenic cells" or "chimeric cells" for the purposes of the invention. Transgenic cells can be useful as materials for nuclear transfer cloning techniques provided herein. The phrase "modified nuclear DNA" may also encompass "heterologous or corrective nucleic acid sequence(s)" which confer a benefit to the cell, e.g., replacement of a mutated nucleic acid molecule with a nucleic acid encoding a biologically active, phenotypically normal polypeptide. The constructs utilized to generate modified nuclear DNA may optionally comprise a reporter gene encoding a detectable product.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, polyA addition signals, transcriptional termination signals and the like.

"Selectable marker" as used herein refers to a molecule that when expressed in cells renders those cells resistant to a selection agent. Nucleic acids encoding selectable markers may also comprise such elements as promoters, enhancers, translational control sequences, polyA addition signals, transcriptional termination signals and the like. Suitable selection agents include antibiotic such as kanamycin, neomycin, and hygromycin.

Methods and tools for insertion, deletion, and mutation of nuclear DNA of mammalian cells are well-known to a person of ordinary skill in the art. See, Molecular Cloning, a Laboratory Manual, 2nd Ed., 1989, Sambrook, Fritsch, and Maniatis, Cold Spring Harbor Laboratory Press; U.S. Pat. No. 5,633,067, "Method of Producing a Transgenic Bovine or Transgenic Bovine Embryo," DeBoer et al., issued May 27, 1997; U.S. Pat. No. 5,612,205, "Homologous Recombination in Mammalian Cells," Kay et al., issued Mar. 18, 1997; and PCT publication WO 93/22432, "Method for Identifying Transgenic Pre-Implantation Embryos"; WO 98/16630, Piedrahita & Bazer, published Apr. 23, 1998, "Methods for the Generation of Primordial Germ Cells and Transgenic Animal Species. These methods include techniques for transfecting cells with foreign DNA fragments and the proper design of the foreign DNA fragments such that they effect insertion, deletion, and/or mutation of the target DNA genome.

Any of the cell types defined herein can be altered to harbor modified nuclear DNA. For example, embryonic stem cells, embryonic germ cells, fetal cells, and any totipotent cell defined herein can be altered to harbor modified nuclear DNA.

Examples of methods for modifying a target DNA genome by insertion, deletion, and/or mutation are retroviral insertion, artificial chromosome techniques, gene insertion, random insertion with tissue specific promoters, homologous recombination, gene targeting, transposable elements, and/or any other method for introducing foreign DNA. Other modification techniques well known to a person of ordinary skill in the art include deleting DNA sequences from a genome, and/or altering nuclear DNA sequences. Examples of techniques for altering nuclear DNA sequences are site-directed mutagenesis and polymerase chain reaction procedures. Therefore, the invention relates in part to mammalian cells that are simultaneously totipotent and transgenic. Such transgenic and totipotent cells can serve as nearly unlimited sources of donor cells for production of cloned transgenic animals.

The term "recombinant product" as used herein can refer to the product produced from a DNA sequence that comprises at least a portion of the modified nuclear DNA. This product can be a peptide, a polypeptide, a protein, an enzyme, an antibody, an antibody fragment, a polypeptide that binds to a regulatory element (a term described hereafter), a structural protein, an RNA molecule, and/or a ribozyme, for example. These products are well defined in the art.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art. In a preferred embodiment, the promoters of the invention drive germ line specific expression of the transgenes described herein. Such promoters include the truncated Oct4 promoter, the GCNA promoter, the c-kit promoter and the mouse Vasa-homologue protein (mvh) promoter.

The term "enhancers" or "enhancer" as used herein can refer to a DNA sequence that is located adjacent to the DNA sequence that encodes a recombinant product. Enhancer elements are typically located upstream of a promoter element or can be located downstream of or within a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

The term "nuclear transfer" as used herein can refer to introducing a full complement of nuclear DNA from one cell to an enucleated cell (e.g. egg). Nuclear transfer methods are well known to a person of ordinary skill in the art. See, e.g., Nagashima et al. (1997) Mol. Reprod. Dev. 48: 339-343; Nagashima et al. (1992) J. Reprod. Dev. 38: 73-78; Prather et al. (1989) Biol. Reprod. 41: 414-419; Prather et al. (1990) Exp. Zool. 255: 355-358; Saito et al. (1992) Assis. Reprod. Tech. Andro. 259: 257-266; and Terlouw et al. (1992) Theriogenology 37: 309. Nuclear transfer may be accomplished by using oocytes that are not surrounded by a zona pellucida.

The term "thawing" as used herein can refer to a process of increasing the temperature of a cryopreserved cell, embryo, or portions of animals. Methods of thawing cryopreserved materials such that they are active after a thawing process are well-known to those of ordinary skill in the art.

The terms "transfected" and "transfection" as used herein refer to methods of delivering exogenous DNA into a cell. These methods involve a variety of techniques, such as treating cells with high concentrations of salt, an electric field, liposomes, polycationic micelles, or detergent, to render a host cell outer membrane or wall permeable to nucleic acid molecules of interest. These specified methods are not limiting and the invention relates to any transformation technique well known to a person of ordinary skill in the art.

The term "antibiotic" as used herein can refer to any molecule that decreases growth rates of a bacterium, yeast, fungi, mold, or other contaminants in a cell culture. Antibiotics are optional components of cell culture media. Examples of antibiotics are well known in the art. See Sigma and DIFCO catalogs.

The term "feeder cells" as used herein can refer to cells that are maintained in culture and are co-cultured with target cells. Target cells can be precursor cells, embryonic stem cells, embryonic germ cells, cultured cells, and totipotent cells, for example. Feeder cells can provide, for example, peptides, polypeptides, electrical signals, organic molecules (e.g., steroids), nucleic acid molecules, growth factors (e.g., bFGF), other factors (e.g., cytokines such as LIF and steel factor), and metabolic nutrients to target cells. Certain cells, such as embryonic germ cells, cultured cells, and totipotent cells may not require feeder cells for healthy growth. Feeder cells preferably grow in a mono-layer.

Feeder cells can be established from multiple cell types. Examples of these cell types are fetal cells, mouse cells, Buffalo rat liver cells, and oviductal cells. These examples are not meant to be limiting. Tissue samples can be broken down to establish a feeder cell line by methods well known in the art (e.g., by using a blender). Feeder cells may originate from the same or different animal species as precursor cells. Feeder cells can be established from ungulate fetal cells, mammalian fetal cells, and murine fetal cells. One or more cell types can be removed from a fetus (e.g., primordial germs cells, cells in the head region, and cells in the body cavity region) and a feeder layer can be established from those cells that have been removed or cells in the remaining dismembered fetus. When an entire fetus is utilized to establish fetal feeder cells, feeder cells (e.g., fibroblast cells) and precursor cells (e.g., primordial germ cells) can arise from the same source (e.g., one fetus).

The term "receptor ligand cocktail" as used herein can refer to a mixture of one or more receptor ligands. A receptor ligand can refer to any molecule that binds to a receptor protein located on the outside or the inside of a cell. Receptor ligands can be selected from molecules of the cytokine family of ligands, neurotrophin family of ligands, growth factor family of ligands, and mitogen family of ligands. Examples of receptor/ligand pairs are: epidermal growth factor receptor/epidermal growth factor, insulin receptor/insulin, cAMP-dependent protein kinase/cAMP, growth hormone receptor/growth hormone, and steroid receptor/steroid. It has been shown that certain receptors exhibit cross-reactivity. For example, heterologous receptors, such as insulin-like growth factor receptor 1 (IGFR1) and insulin-like growth factor receptor 2 (IGFR2) can both bind IGF1. When a receptor ligand cocktail comprises a stimulus, the receptor ligand cocktail can be introduced to a precursor cell in a variety of manners known to a person of ordinary skill in the art.

The term "cytokine" as used herein refers to a large family of receptor ligands. The cytokine family of receptor ligands includes such members as leukemia inhibitor factor (LIF); cardiotrophin 1 (CT-1); ciliary neurotrophic factor (CNTF); stem cell factor (SCF), which is also known as Steel factor; oncostatin M (OSM); and any member of the interleukin (IL) family, including IL-6, IL-1, and IL-12. The teachings of the invention do not require the mechanical addition of steel factor (also known as stem cell factor in the art) for the conversion of precursor cells into totipotent cells.

The term "cloned" as used herein can refer to a cell, embryonic cell, fetal cell, and/or animal cell having a nuclear DNA sequence that is substantially similar or identical to a nuclear DNA sequence of another cell, embryonic cell, fetal cell, and/or animal cell. A cloned embryo can arise from one nuclear transfer process, or alternatively, a cloned embryo can arise from a cloning process that includes at least one re-cloning step. Additionally, a clone embryo may arise by the splitting of an embryo (e.g. the formation of monozygotic twins). If a cloned embryo arises from a cloning procedure that includes at least one re-cloning step, then the cloned embryo can indirectly arise from a totipotent cell since the re-cloning step can utilize embryonic cells isolated from an embryo that arose from a totipotent cell.

The term "implanting" refers to impregnating a female animal with an embryo as described herein. Implanting techniques are well known by the skilled person. See, e.g., Polge & Day, 1982, "Embryo transplantation and preservation," Control of Pig Reproduction, DJA Cole and GR Foxcroft, eds., London, UK, Butterworths, pp. 227-291; Gordon, 1997, "Embryo transfer and associated techniques in pigs," Controlled reproduction in pigs (Gordon, ed), CAB International, Wallingford UK, pp 164-182; and Kojima, 1998, "Embryo transfer," Manual of pig embryo transfer Procedures, National Livestock Breeding Center, Japanese Society for Development of Swine Technology, pp 76-79. The embryo may be allowed to develop in utero, or alternatively, the fetus may be removed from the uterine environment before parturition.

The term "nuclear donor" as used herein can refer to a cell or a nucleus from a cell that is translocated into a nuclear acceptor. A nuclear donor may be a totipotent mammalian cell. In addition, a nuclear donor may be any cell described herein, including, but not limited to a non-embryonic cell, a non-fetal cell, a differentiated cell, a somatic cell, an embryonic cell, a fetal cell, an embryonic stem cell, a primordial germ cell, a genital ridge cell, a cumulus cell, an amniotic cell, a fetal fibroblast cell, a hepatacyte, an embryonic germ cell, an adult cell, a cell isolated from an asynchronous population of cells, and a cell isolated from a synchronized population of cells where the synchronous population is not arrested in the G0 stage of the cell cycle. A nuclear donor cell can also be a cell that has differentiated from an embryonic stem cell. See, e.g., Piedrahita et al. (1998) Biol. Reprod 58: 1321-1329; Shim et al. (1997) Biol. Reprod. 57: 1089-1095; Tsung et al. (1995) Shih Yen Sheng Wu Hsueh Pao 28: 173-189; and Wheeler (1994) Reprod Fertil. Dev. 6: 563-568. In addition, a nuclear donor may be a cell that was previously frozen or cryopreserved.

The term "enucleated oocyte" as used herein can refer to an oocyte which has had its nucleus or its chromosomes removed. Typically, a needle can be placed into an oocyte and the nucleus and/or chromosomes can be aspirated into the needle. The needle can be removed from the oocyte without rupturing the plasma membrane. This enucleation technique is well known to a person of ordinary skill in the art. See, e.g., U.S. Pat. No. 4,994,384; U.S. Pat. No. 5,057,420; and Willadsen, 1986, Nature 320:63-65. If the oocyte is obtained in an immature state (e.g. as with current bovine techniques), an enucleated oocyte is prepared from an oocyte that has been matured for greater than 24 hours, preferably matured for greater than 36 hours, more preferably matured for greater than 48 hours, and most preferably matured for about 53 hours.

The terms "maturation" and "matured" as used herein can refer to a process in which an oocyte is incubated in a medium in vitro, typically until the stage at which natural fertilization occurs. Maturation media can contain multiple types of components, including hormones and growth factors. Time of maturation can be determined from the time that an oocyte is placed in a maturation medium to the time that the oocyte is subject to a manipulation (e.g., enucleation, nuclear transfer, fusion, and/or activation). Oocytes can be matured in multiple media as described in the following references. See, e.g., Mattioli et al. (1989) Theriogenology 31: 1201-1207; Jolliff & Prather, (1997) Biol. Reprod. 56: 544-548; Funahashi & Day (1993) J. Reprod. Fert. 98: 179-185; Nagashima et al. (1997) Mol. Reprod. Dev. 38: 339-343; Abeydeera et al. (1998) Biol. Reprod. 58: 213-218; Funahashi et al. (1997) Biol. Reprod. 57: 49-53; and Sawai et al. (1997) Biol. Reprod. 57: 1-6. Oocytes can be matured for any period of time: an oocyte can be matured for greater than 10 hours, greater than 20 hours, greater than 24 hours, greater than 60 hours, greater than 72 hours, greater than 90 hours, preferably matured for greater than 36 hours, more preferably matured for greater than 48 hours, and most preferably matured for about 53 hours. The term "about" with respect to oocyte maturation can refer to plus or minus 3 hours.

The term "injection" as used herein in reference to embryos, can refer to perforation of an oocyte with a needle, and insertion of a nuclear donor in the needle into the oocyte. In preferred embodiments, a nuclear donor may be injected into the cytoplasm of an oocyte or in the perivitelline space of an oocyte. For a direct injection approach to nuclear transfer, a whole cell may be injected into an oocyte, or alternatively, nuclear DNA or a nucleus isolated from a cell may be injected into an oocyte. Such an isolated nucleus may be surrounded by nuclear membrane only, or the isolated nucleus may be surrounded by nuclear membrane and plasma membrane in any proportion. An oocyte may be pre-treated by any of a variety of known techniques which improve the survival rate of the oocyte after nuclear injection, such as by incubating the oocyte in sucrose prior to injection of a nuclear donor.

The term "electrical pulses" as used herein can refer to subjecting a nuclear donor and recipient oocyte to electric current. For nuclear transfer, a nuclear donor and recipient oocyte can be aligned between electrodes and subjected to electrical current. Electrical current can be alternating current or direct current. Electrical current can be delivered to cells for a variety of different times as one pulse or as multiple pulses. Cells are typically cultured in a suitable medium for delivery of electrical pulses. Examples of electrical pulse conditions utilized for nuclear transfer are well known in the art.

The term "fusion agent" as used herein can refer to any compound or biological organism that can increase the probability that portions of plasma membranes from different cells will fuse when a nuclear donor is placed adjacent to a recipient oocyte. In preferred embodiments fusion agents are selected from the group consisting of polyethylene glycol (PEG), trypsin, dimethylsulfoxide (DMSO), lectins, agglutinin, viruses, and Sendai virus. These examples are not meant to be limiting and other fusion agents known in the art are applicable and included herein.

The term "activation" can refer to any materials and methods useful for stimulating a cell to divide before, during, and after a nuclear transfer step. The term "cell" as used in the previous sentence can refer to an oocyte, a nuclear donor, and an early stage embryo. These types of cells may require stimulation in order to divide after nuclear transfer has occurred. The invention pertains to any activation materials and methods known to a person of ordinary skill in the art.

Examples of components that are useful for non-electrical activation include ethanol; inositol trisphosphate ($IP_3$); divalent ions (e.g., addition of $Ca^{2+}$ and/or $Sr^{2+}$); microtubule inhibitors (e.g., cytochalasin B); ionophores for divalent ions (e.g., the a³⁺ionophore ionomycin); protein kinase inhibitors (e.g., 6-dimethylaminopurine (DMAP)); protein synthesis inhibitors (e.g., cyclohexamide); phorbol esters such as phorbol 12-myristate 13-acetate (PMA); and thapsigargin. It is also known that temperature change and mechanical techniques are also useful for non-electrical activation. The invention includes any activation techniques known in the art. See, e.g., U.S. Pat. No. 5,496,720, entitled "Parthenogenic Oocyte Activation," issued on Mar. 5, 1996, Susko-Parrish et al., and Wakayama et al. (1998) Nature 394: 369-374.

When ionomycin and DMAP are utilized for non-electrical activation, ionomycin and DMAP may be introduced to cells simultaneously or in a step-wise addition, the latter being a preferred mode.

The term "inner cell mass" as used herein can refer to cells within the blastocyst that give rise to the embryo proper. Cells that line the outside of a blastocyst can be referred to as a trophoblast of the embryo. Methods for isolating inner cell mass cells from an embryo are well known to a person of ordinary skill in the art, as discussed previously. The term "pre-blastocyst" is well known in the art and is referred to previously.

In one embodiment of the invention, a new approach for the enucleation of a cell, specifically an oocyte, is described. This method entails exposing the oocyte to an agent that inhibits tubulin polymerization or causes tubulin depolymerization such that the mitotic spindle is disrupted. Such spindle disrupting agents include, without limitation, nocodazole, demecolcine, colcemid, and colchicine. Preferably, nocodazole is employed because, in part, of its lower toxicity to oocytes. Typically, the oocyte is also exposed to agents that inhibit actin polymerization which reduce the likelihood of the oocyte from rupturing from the manipulation of the oocyte to remove the chromosomes. Such actin polymerization inhibitors include, but are not limited to, cytochalasin B and cytochalasin D. The chromosomes of the oocyte are removed after incubation in the above-identified agents by micromanipulation techniques well-known in the art and described hereinabove.

This method of enucleation specifically removes the chromosomes while leaving most of the associated materials in place. Removal of essentially only the chromosomes facilitates superior cell division and development thereby producing more clones with a higher cell number prior to implantation. Notably, recent attempts in primate cell nuclear transfer implicate the requirements of spindle associated factors in effective cloning procedures (Simerly, C. et al. (2003) Science 300:297; Vogel, G. et al. (2003) Science 300:225-227).

In another embodiment of the invention, culture techniques for increasing the number of nucleus-transferred oocytes which successfully form blastocysts are provided. Specifically, embryos, in particular clone embryos, are obtained by the activation of a nucleus-transferred oocyte or by any other method known in the art. Clone embryos are then combined with one another before the stage when Oct4 is expressed in normal development (i.e., the morula stage). The zona pellucida is removed from the embryos (typically at the 4-cell stage) and then the zona-free embryos are combined to form "homologous aggregations" of two, three, four or more clone embryos identical with one another. The zona pellucida can be removed by any means known in the art such as, without limitation, treatment with acidic Tyrode's solution or pronase or by physical manipulation by means of a micro-needle, laser, or the like. Preferably, the clones of the aggregation are genetically identical although not necessarily epigenetically identical. Clone aggregates can be derived from different cell types of the same individual. The aggregation of clone embryos has at least two immediate benefits. The first is that the aggregation increases the cell number, which is characteristically low in clone embryos as currently generated by the Roslin and Honolulu methods. For example, clones at the blastocyst stage from several species (55% lower in mouse, 43% in rabbit, 19% in porcine, 9% in bovine) exhibit a lower cell number than controls and cavitate later than controls (Chung, YG et al. (2002) Biol Reprod. 66:1178-84; Chesne, P. et al. (2002) Nat Biotechnol. 20:366-9; Koo, DB et al. (2002) Biol Reprod. 67:487-92; Koo, DB et al. (2000) Biol. Reprod. 63:986-92). The second benefit is improved gene expression within the clone embryo. Gene expression is typically mosaic and irregular in clone embryos as currently generated by the Roslin and Honolulu methods. As nuclear reprogramming occurs throughout embryo cleavage, formation of the embryo aggregates enhances regulated, "normal" gene expression.

Uses of the Blastocysts of the Invention in Methods for Therapeutic Cloning

The embryo aggregates of the present invention have increased biomass and excess nuclear cytoplasmic factors which facilitate appropriate gene expression and blastocyst formation which is correlated with the enhanced viability of such embryos. The ability to efficiently obtain clone blastocysts from donated oocytes and individual-specific somatic cells provides the means to reproducibly generate replacement cells or tissues which are useful in therapeutic cloning protocols. In such protocols, obtained oocytes are enucleated as set forth above. Somatic cell nuclei are obtained from the patient to be treated and somatic cell transfer is then performed. If the patient to be treated has a genetic mutation that is undesirable, the somatic cells utilized for nuclear transfer may optionally be transformed with a "heterologous or corrective nucleic acid sequence" which corrects the underlying genetic defect. These cells are transformed into clone blastocysts by nuclear transfer, from which transgenic stem cells may then be isolated. Transgenic stem cells so obtained may also be optionally manipulated at this point with a "corrective nucleic acid sequence". The resulting stem cells are then passaged and exposed to a receptor ligand cocktail to induce differentiation into the desired cell lineage as exemplified hereinbelow.

Tissues currently being developed from stem cells include, but are not limited to: blood vessels (Kocher, A. A. et al., Nature Med. (2001) 7:430-436; Jackson, K. A. et al., J. Clin. Invest. (2001) 107:1395-1402), bone (Petite, H. et al., Nature Biotech. (2000) 18:959-963), cartilage (Johnstone, B. et al., Clin. Orthop. (1999) S156-S162), cornea (Tsai, R. J. et al., N. Eng. J. Med. (2000) 343:86-93), dentin (Gronthos, S. et al., Proc. Natl. Acad. Sci. USA (2000) 97:13625-13620), heart muscle (Klug, M. G. et al., J. Clin. Invest. (1996) 98:216-224; review Boheler, K. R. et al., Cir. Res. (2002) 91:189-201), liver (Lagasse, E. et al., Nature Med. (2000) 6:1229-1234), pancreas (Soria, B. et al., Diabetes (2000) 49:1-6; Ramiya, V. K. et al., Nature Med. (2000) 6:278-282), nervous tissue (Bjorkland, A., Novaritis Found. Symp. (2000) 231:7-15; Lee, S. H. et al., Nature Biotechnology, (2000) 18:675-679; Kim, J. H. et al., Nature (2002) 418:50-56), skeletal muscle (Gussoni, E. et al., Nature (1999) 401:390-394), and skin (Pellegrini, G. et al., Transplantation (1999) 68:868-879). Protocols for the differentiation of certain tissue types from stem cells are described in further detail below.

Neuronal Cells

Parkinson's disease is caused by the loss of midbrain neurons that synthesize the neurotransmitter dopamine. Delivery of dopamine-synthesizing neurons to the midbrain should alleviate the symptoms of the disease by restoring dopamine production. Stem cells obtained using the methods of the invention may be differentiated into dopamine-synthesizing neurons utilizing the protocols set forth below. (Lee, S. H. Yet al., Nature Biotechnology, (2000) 18:675-679; Kim, J. H. et al., Nature (2002) 418:50-56).

In a murine model, mouse ES cells were first transfected by electroporation with a plasmid expressing nuclear receptor related-1 (Nurr1), a transcription factor that has a role in the differentiation of midbrain precursors into dopamine neurons and a plasmid encoding neomycin resistance. Transfected clones (Nurr1 ES cells) were then subsequently isolated by culturing the cells in G418. The Nurr1 ES cells were then expanded under cultures which prevented differentiation (e.g., growth on gelatin-coated tissue culture plates in the presence of 1,400 U/ml-l of leukemia inhibitory factor (LIF; GIBCO/BRL, Grand Island, N.Y.) in ES cell medium consisting of knockout Dulbecco's minimal essential medium (GIBCO/BRL) supplemented with 15% FCS, 100 mM MEM nonessential amino acids, 0.55 mM 2-mercaptoethanol, L-glutamine, and antibiotics (all from GIBCO/BRL)). To induce EB formation, the cells were dissociated into a single-cell suspension by 0.05% trypsin and 0.04% EDTA in PBS and plated onto nonadherent bacterial culture dishes at a density of $2\text{-}2.5\times10^4$ cells/cm$^2$ in the medium described above. The EBs were formed for four days and then plated onto adhesive tissue culture surface in the ES cell medium. After 24 hours of culture, selection of nestin-positive cells, a marker of developmental neuorns, was initiated by replacing the ES cell medium by serum-free Dulbecco's modified Eagle's medium (DMEM)/F12 (1:1) supplemented with insulin (5 μg/ml), transferrin (50 μg/ml), selenium chloride (30 nM), and fibronectin (5 μg/ml) (ITSFn) medium. After 6-10 days of selection, expansion of nestin-positive cells was initiated. Specifically, the cells were dissociated by 0.05% trypsin/0.04% EDTA, and plated on tissue culture plastic or glass coverslips at a concentration of $1.5\text{-}2\times10^5$ cells/cm$^2$ in N2 medium modified (described in Johe, K. et al., Genes Dev. (1996) 10:3129-3140), and supplemented with 1 μg/ml of laminin and 10 ng/ml of bFGF (R&D Systems, Minneapolis, Minn.) in the presence of murine N-terminal fragment of sonic hedgehog (SHH; 500 ng/ml) and murine fibroblast growth factor (FGF) 8 isoform b (100 ng/ml; both from R&D Systems). Before cell plating, dishes and coverslips were precoated with polyornithine (15 mg/ml) and laminin (1 μg/ml, both from Becton Dickinson Labware, Bedford, Mass.). Nestin-positive cells were again expanded for six days. The medium was changed every two days. Differentiation was induced by removal of basic fibroblast growth factor (bFGF). The differentiation medium consisted of N2 medium supplemented with laminin (1 mg/ml) in the presence of cAMP (1 μM) and ascorbic acid (200 μM, both from Sigma, St. Louis, Mo.). The cells were incubated under differentiation conditions for 6-15 days. 78% of Nurr1 ES cells were found to be induced into dopamine-synthesizing, tyrosine hydroxylase (TH, a rate limiting enzyme in the biosynthesis of dopamine) positive neurons by the method set forth above. The resultant neurons were further characterized to express a variety of midbrain-specific markers such as Ptx3 and Engrailed 1 (En-1). The dopamine-synthesizing, TH+ cells were also grafted into a rodent model of Parkinson's disease and were shown to extend axons, form functional synaptic connections, perform electrophysiological functions expected of neurons, innervate the striatum, and improve motor asymmetry.

Heart Muscle

The loss of cardiomyocytes from adult mammmalian hearts is irreversible and leads to diminished heart function. Methods have been developed in which ES cells are employed as a renewable source of donor cardiomyocytes for cardiac engraftment (Klug, M. G. Yet al., J. Clin. Invest. (1996) 98:216-224).

ES cells were first transfected by electroporation with a plasmid expressing the neomycin resistance gene from an α-cardiac myosin heavy chain promoter and expressing the hygromycin resistance gene under the control of the phosphoglycerate kinase (pGK) promoter. Transfected clones were selected by growth in the presence of hygromycin (200 μg/ml; Calbiochem-Novabiochem). Transfected ES cells were maintained in the undifferentiated state by culturing in high glucose DMEM containing 10% fetal bovine serum (FBS), 1% nonessential amino acids, and 0.1 mM 2-mercaptoethanol. The medium was supplemented to a final concentration of 100 U/ml with conditioned medium containing recombinant LIF.

To induce differentiation, $2\times10^6$ freshly dissociated transfected ES cells were plated onto a 100-mm bacterial Petri dish containing 10 ml of DMEM lacking supplemental LIF. After 3 days in suspension culture, the resulting EBs were plated onto plastic 100-mm cell culture dishes and allowed to attach. Regions of cardiogenesis were readily identified by the presence of spontaneous contractile activity. For cardiomyocyte selection, the differentiated cultures were grown for 8 days in the presence of G418 (200 μg/ml; GIBCO/BRL). Cultures of selected ES-derived cardiomyocytes were digested with trypsin and the resulting single cell preparation was washed three times with DMEM and directly injected into the ventricular myocardium of adult mice.

The culture obtained by this method after G418 selection is approximately 99% pure for cardiomyocytes based on immunofluorescence for myosin. The obtained cardiomyocytes contained well-defined myofibers and intercalated discs and were observed to couple juxtaposed cells consistent with the observation that adjacent cells exhibit synchronous contractile activity. Importantly, the selected cardiomyocytes were capable of forming stable intercardiac grafts with the engrafted cells aligned and tightly juxtaposed with host cardiomyocytes.

Insulin-Producing Cells

An ideal treatment for diabetes is the restoration of β-cell function or mimicking the insulin secretory pattern of these cells. Insulin-secreting cells derived from ES cells have been generated by the following method and have been shown to be capable of normalizing blood glucose levels in a diabetic mouse model (Soria, B. et al., Diabetes (2000) 49:1-6).

ES cells were transfected by electroporation with a plasmid expressing β-gal under the control of the human insulin regulatory region and expressing the hygromycin resistance gene under the control of the pGK promoter. Transfected clones were selected by growth in the presence of hygromycin (200 μg/ml; Calbiochem-Novabiochem). Transfected ES cells were maintained in the undifferentiated state by culturing in high glucose Dulbecco's modified Eagle's medium (DMEM) containing 10% fetal bovine serum (FBS), 1% nonessential amino acids, 0.1 mM 2-mercaptoethanol, 1 mM sodium pyruvate, 100 IU/ml penicillin, and 0.1 mg/ml streptomycin. The medium was supplemented to a final concentration of 100 U/ml with conditioned medium containing recombinant LIF.

To induce differentiation to an insulin-secreting cell line, $2\times10^6$ hygromycin-resistant ES cells were plated onto a 100-mm bacterial Petri dish and cultured in DMEM lacking supplemental LIF. After 8-10 days in suspension culture, the resulting EBs were plated onto plastic 100-mm cell culture dishes and allowed to attach for 5-8 days. For ES Ins/β-gal selection, the differentiated cultures were grown in the same medium in the presence of 200 μg/ml G418. For final differentiation and maturation, the resulting clones were trypsinized and plated on a 100-mm bacterial Petri dish and grown for 14 days in DMEM supplemented with 200 μg/ml G418 and 10 mM nicotinamide (Sigma), a form of Vitamin B3 that may preserve and improve beta cell function. Finally, the resulting clusters were cultured for 5 days in RPMI 1640 media supplemented with 10% FBS, 10 mM nicotinamide, 200 μg/ml G418, 100 IU/ml penicillin, 0.1 mg/ml streptomycin, and low glucose (5.6 mM).

For cell implantation, ES-derived insulin-secreting cells were washed and resuspended in RPMI 1640 media supplemented with 10% FBS, 10 mM nicotinamide, 100 IU/ml penicillin, 0.1 mg/ml streptomycin, and 5.6 mM glucose at $5 \times 10^6$ cells/ml. The mice to receive the implantation of ES-derived insulin-secreting cells were male Swiss albino mice that had diabetic conditions induced by a single intraperitoneal injection of streptozotocin (STZ, Sigma) at 200 mg/kg body weight in citrate buffer. $1 \times 10^6$ cells were injected into the spleen of mice under anesthesia.

The ES-derived insulin-secreting cells produced from this method produced a similar profile of insulin production in response to increasing levels of glucose to that observed in mouse pancreatic islets. Significantly, implantation of the ES-derived insulin-secreting cells led to the correction of the hyperglycemia within the diabetic mouse, minimized the weight loss experienced by the mice injected with STZ, and lowered glucose levels after meal challenges and glucose challenges better than untreated diabetic mice and similar to control nondiabetic mice.

Human ES Cells

While the preceding examples describe the manipulation of murine ES cells, the current invention also encompasses the manipulation of human ES cells and the use of the same in the therapeutic cloning protocols described above. The technology for manipulating human ES cells is quite similar to the manipulation of murine ES cells, except that human ES cells do not require leukemia inhibitory factor (LIF) and can divide while maintaining plutipotency far beyond their murine counterparts as the following example demonstrates (Schuldiner, M. et al., Proc. Natl Acad. Sci. USA (2000) 97:11307-11312). Also see U.S. patent application Ser. No. 2002/0146,678.

Human ES cells, which have been recently derived, are maintained on mitotically inactivated mouse embryo fibroblasts (MEFs) in 80% KnockOut DMEM (an optimized DMEM for ES cells; GIBCO/BRL), 20% KnockOut SR (a serum-free formulation; GIBCO/BRL), 1 mM glutamine, 0.1 mM 2-mercaptoethanol, 1% nonessential amino acids, 4 ng/ml bFGF, and $10^3$ units/ml LIF which helps maintain the cells in an undifferentiated state. To induce formation of EBs, human ES cells were transferred by using 0.1%/1mM trypsin/EDTA to plastic Petri dishes to allow their aggregation and prevent adherence to the plate. Human EBs were grown in the same culture medium, except that it lacked LIF and bFGF. The EBs were cultured for 5 days and then dissociated with trypsin and plated on tissue culture plates coated with 50 μg/ml Fibronectin (Boehringer Mannheim). The ES cells were induced to differentiate by growing in the presence of the following human recombinant growth factors: bFGF (10 ng/ml;GIBCO/BRL), transforming growth factor-β1 (TGF-β1; 2 ng/ml; R&D Systems), activin-A (20 ng/ml; R&D Systems), bone morphogenic protein 4 (BMP-4; 10 ng/ml; R&D Systems), hepatocyte growth factor (HGF; 20 ng/ml; R&D Systems), epidermal growth factor (EGF: 100 ng/ml; R&D Systems), β nerve growth factor (NGF; 100 ng/ml; R&D Systems), or retinoic acid (RA; 1 μM; Sigma). The cells were allowed to differentiate for another 10 days under these conditions. These various treatments resulted in the differentiation of the human ES cells into all three embryonic germ layers: mesoderm, endoderm, and ectoderm. Further treatments of the cells with RA and βNGF were capable of increasing the percentage of cells expressing neuronal cell specific markers (Schuldiner, M., Brain Res. (2001) 913:201-205).

One such example of the production of a specific differentiated cell is that of the formation of cardiomyocytes from human ES cells (Kehat, I., J. Clin. Invest. (2001) 108:407-414). Briefly, human ES cells were grown on mitotically inactivated MEF feeder cells in culture medium consisting of 80% KnockOut DMEM, 20% FBS, 1 mM glutamine, 0.1 mM 2-mercaptoethanol, and 1% nonessential amino acids. To induce differentiation, ES cells were dispersed into small clumps using 1 mg/ml collagenase IV (Life Technologies Inc.). The cells were then transferred to plastic Petri dishes where they were cultured in suspension for 7-10 days. The formed EBs were then plated onto 0.1% gelatin-coated culture dishes. The EBs were observed microscopically and approximately 8% of the EBs contained spontaneously contracting areas reminiscent of cardiomyocytes. Significantly, the spontaneously contracting cells expressed a number of cardiac-restricted gene products and transcription factors, displayed electro-physiological properties similar to that of early cardiomyocytes, and exhibited structural features consistent with early-stage cardiac tissue.

Additionally, the recently described ability to genetically manipulate human ES cells should allow for the rapid isolation of highly uniform and singularly differentiated cells (Eiges, R. et al., Current Biol. (2001) 11:514-518). A potential method to this end would be to employ a similar method to that described above for murine ES cells in which antibiotic resistance genes or selectable marker genes are expressed under cell specific promoters. Alternatively, cell-type specific transcription factors or any other cell-type specific factors found to drive cell-type specific differentiation can be expressed. Briefly, the method of genetically manipulating human ES cells entails culturing human ES cells on mitotically inactivated MEF feeder cells in culture medium consisting of 80% KnockOut DMEM, 20% KnockOut SR, 1 mM glutamine, 0.1 mM 2-mercaptoethanol, 1% nonessential amino acids, 50 μg/ml streptomycin, 4 ng/ml bFGF, and $10^3$ units/ml LIF. The cells were then transfected with a plasmid expressing neomycin resistance under the control of an SV40 promoter and green fluorescent protein (GFP) under the control of a promoter that functions in undifferentiated cells. The method of transfection was the chemical transfection reagent ExGen 500 (Fermentas) as human ES cells do not survive electroporation well. Residual transfection reagent is washed away 1 hour later and one day later cells are trypsinized and plated on 100-mm culture dishes containing inactivated $MEF^{Neo+}$ cells. Two days post-replating, G418 (200 ng/ml) was added to the growth medium allowing for selective propagation. At two weeks after selection, over 80% of neomycin resistant cells were found to express GFP. The transfected ES cells were also shown to be capable of forming EBs by removal of bFGF and LIF and allowing aggregation in Perti dishes.

Uses of the Blastocysts of the Invention in Methods for Reproductive Cloning of Non-Human Animals To date, sheep, cattle, goats, cats, rabbits, mice and pigs have been cloned successfully. The ability to efficiently generate more clone embryos and embryos of a higher quality grade in accordance with the present invention, facilitates the production of cloned non-human animals which possess genetically superior phenotypic traits. Indeed, the methods of the instant invention have proved effective in cloning mice, which are typically considered a hard to clone species. The methods of the instant invention can also be readily employed in the methods of cloning species already cloned and those yet to be cloned.

The following patent documents provide some examples of methods for cloning animals in which the methods of the instant invention could be employed to enhance efficiency and success rates: U.S. Pat. No. 6,258,998 entitled "Methods for cloning porcine animals"; U.S. Pat. No. 6,107,543 "Culture of totipotent embryonic inner cell mass cells and production of bovine animals"; U.S. Pat. No. 6,147,276, "Quiescent cell populations for nuclear transfer in the production of non-human mammals and non-human mammalian embryos" and U.S. Pat. No. 6,215,041 "Cloning using donor nuclei from non-quiescent somatic cells." Given the disclosures of the foregoing patents, the skilled person is readily able to effectively generate non-human animals using the methods provided herein.

The following examples provide illustrative methods of practicing the instant invention, and are not intended to limit the scope of the invention in any way.

EXAMPLE 1

Production Of Clone Blastocysts

For cloning purposes, 8-12 week old B6C3F1 females (C3 mice; Taconic, Germantown, N.Y.) were used as oocyte donors and 6-24 week old B6OG2F1 females (OG2 mice; provided by Jeffrey Mann; described in Szabo et al. (2002) Mech. Dev. 115:157-160) were used as nucleus donors. OG2 mice carry an Oct4-GFP (green fluorescent protein) transgene that is expressed in the pluripotent cell lineages. All mice were kept in a colony room under controlled temperature (20° C.) and photoperiod (0800-2000 light hours) and fed Harlan Teklad chow (low phytosterol content; Madison, Wis.).

Oocytes were recovered from C3 mice after gonadotropin stimulation with 10 units each of pregnant mare serum gonadotropin (PMSG; Calbiochem, San Diego Calif.) and human chorionic gonadotropin (hCG, Calbiochem) intraperitoneally 48 hours apart. After the induced superovulation, the oviducts were dissected and the cumulus-oocyte masses were released in Hepes-buffered CZB (Chatot-Ziomek-Bavister; Chatot, C. L. Yet al. (1989) J. Reprod. Fertil. 86:679-688; Table 1) medium containing glucose 1 g/L, 0.1% w/v polyvynilpyrrolidone (PVP; Calbiochem), and no albumin. This medium was prepared in 95% the standard volume thereby rendering the solution hypertonic.

TABLE 1

| Component | Supplier | CZB (mg/L) | α-MEM (mg/L) |
|---|---|---|---|
| Gas phase | | Air | 5% $CO_2$ |
| $NaH_2PO_4$ | EM Science | | 140 |
| $KH_2PO_4$ | Calbiochem | 162 | |
| $CaCl_2\ 2H_2O$ | Calbiochem | 250 | 265 |
| $MgSO_4\ 7H_2O$ | Calbiochem | 290 | 200 |
| Cl | Calbiochem | 4760 | 6800 |
| KCl | Calbiochem | 360 | 400 |
| D(+)glucose | Calbiochem | 1000 | 1000 |
| Na-pyruvate | Sigma | 36 | 110 |
| Na-lactate | Sigma | 5.3 ml | |
| Hepes 4-(2-hydroxyehtyl)-1-piperazineethanesulfonic acid | EM Science | 4760 | |
| $NaHCO_3$ | Fisher Scientific | 420 | 2200 |
| Non-essential amino acids | Sigma | | 1X |
| Essential amino acids | Sigma | | 1X |
| Vitamins | Sigma | | 1X |
| PVP, 40 KDa | Calbiochem | 1000-10000 | |
| Bovine serum albumin, fraction V | Serological Corporations | | 4000 |

The cumulus masses were transferred into drops of hyaluronidase solution (Calbiochem) made in Hepes buffered CZB medium at a working concentration of 50 U/ml. After 20 to 30 minutes at 28° C., the dispersed cumulus cells were stored at 4° C. until used as donor cells (when OG2 mice were employed in the described procedure). The hyaluronidase was washed from the cumulus-free oocytes which were subsequently incubated in culture medium (α-MEM (Sigma, St. Louis, Mo.) supplemented with 0.4% w/v albumin (ICN, Irvine, Calif.) and prepared in 20 μl drops under silicon oil (Sigma)) in 5% $CO_2$ atmosphere at 37° C.

Figure 1:
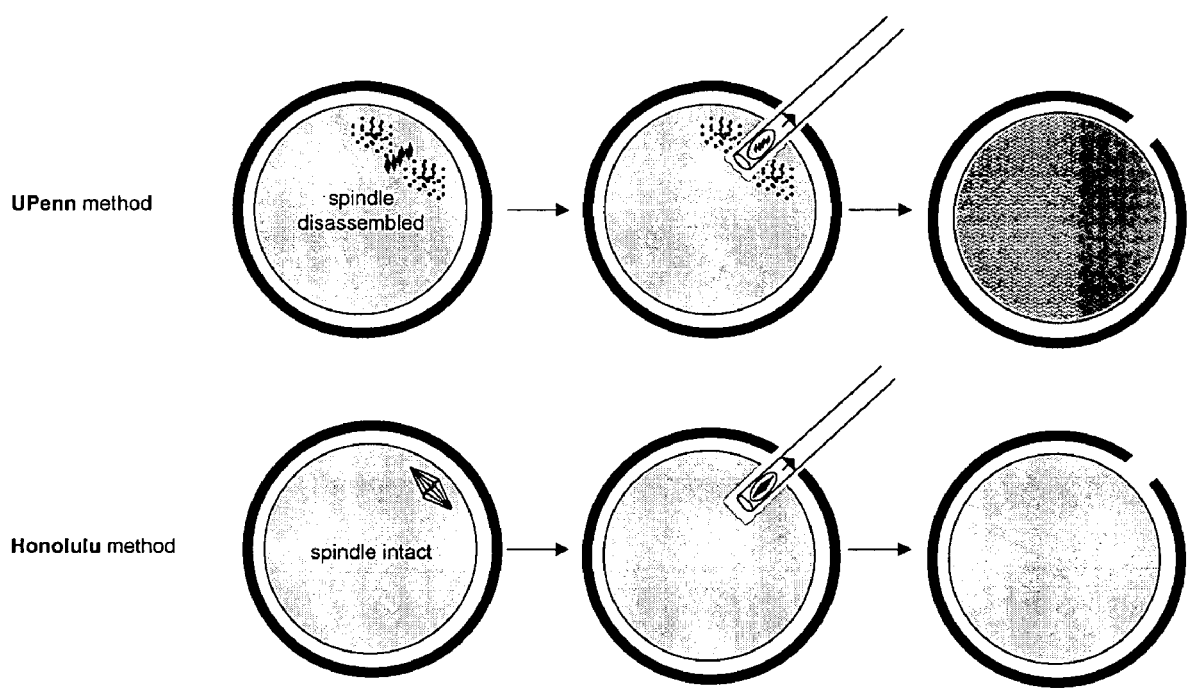
FIG. 1 is a schematic drawing depicting the difference between the enucleation method described in the instant invention (Upenn method) and the Honolulu method.

The oocytes were enucleated (FIG. 1) in batches of 20 over the course of 2.5 hours. The oocytes were placed in Hepes-buffered CZB medium (prepared in 95% the standard volume) supplemented with both 0.25 μg/ml cytochalasin B (ICN; stock solution of 5 μg/μl in dimethyl sulfoxide, DMSO) and 0.5 μg/ml nocodazole (ICN) for 10-15 minutes prior to enucleation. Micromanipulation was performed at 28° C. under an inverted microscope (Nikon Eclipse 2000U) fitted with differential interference contrast (DIC) extended long working distance (ELWD) optics. The microscope was equipped with a manual micromanipulator (Narishige MN-188NE) and a piezo unit (PrimeTech PMAS-CT150). The use of such optics in combination with glass-bottomed vessels obviated the need to stain chromosomes with a dye specific for DNA (e.g. Hoescht 33342) in order to remove the metaphase chromosomes (i.e. enucleation). Oocytes were immediately transferred to culture medium and rinsed several times after enucleation.

The transplantation of nuclei into the oocytes took place one hour after the last batch of oocytes had undergone enucleation. A microcapillar injection needle (8-10 μm inner diameter), back-loaded with mercury, was used for the microinjections. Both the oocytes and the cumulus cells were processed into the same drop of Hepes-buffered CZB medium in the presence of 1% w/v PVP. This medium was prepared in 90% the standard volume thereby rendering the solution hypertonic. The hypertonic solution required the pre-equilibration of the oocytes with the solution to avoid floating. The cumulus cells overcame the higher density of the solution and sank to the bottom by virtue of their previous incubation in the cold. Approximately 30-40 donor cumulus cells were sucked into the injection needle while applying piezo pulses and their nuclei were injected one by one into the oocytes. The piezo parameters were set as follows: speed 2, intensity 3 to aspirate cumulus cells; speed 2, intensity 2-3 to drill the zona pellucida; speed 1, intensity 1 to penetrate the oolema. The nuclear injections were conducted on batches of 30 oocytes and were typically performed in less than 15 minutes.

The injected oocytes were incubated in the same dish for 10 minutes to allow for recovery. The oocytes were then passaged into a 1:1 mixture of α-MEM and Hepes-buffered CZB at room temperature for 30 minutes and subsequently incubated in culture medium with albumin. Activation of the reconstructed oocytes started at least one hour, but no more than 2.5 hours, after the last batch of oocytes had been injected with nuclei. The activation of the oocytes was performed by exposing the oocytes to 10 mM $SrCl_2$ (Sigma) in Ca-free M16 medium with 5 μg/ml cytochalasin B to prevent pseudo polar body extrusion. Particular care was taken to remove calcium through passages in pre-activation drops of Ca-free M16 medium. Six hours after the activation has started, the oocytes were washed thoroughly in 3% albumin in culture medium (with calcium) and incubated in culture medium. Cleavage was allowed to occur in 20 μl droplets of culture medium. An equal volume of culture medium was added to the same drop on day 2. The incubation drop or the medium is not changed, but replenished by adding the same medium to the same drop. Blastocysts form by day 4 and can be collected and used for implantation or differentiated on feeder cells in the presence of leukemia inhibiting factor (LIF; 1000 U/ml) so as to enable the formation of ES cells by days 6-7. Ninety percent of oocytes comprising donor nuclei were able to cleave to the 4-cell stage using the method of the invention.

EXAMPLE 2

Homologous Aggregation of 4-Cell Clones

Figure 2:
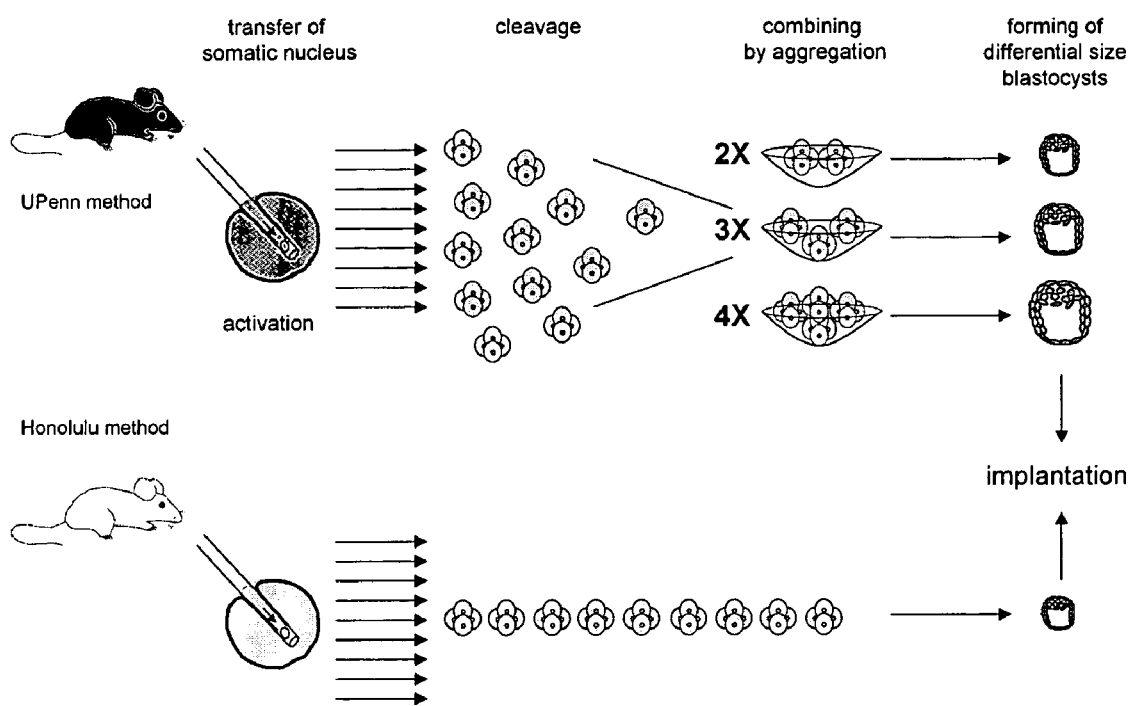
FIG. 2 is a schematic drawing depicting the difference between the cloning method described in the instant invention (Upenn method) and the Honolulu method.
Figure 3:
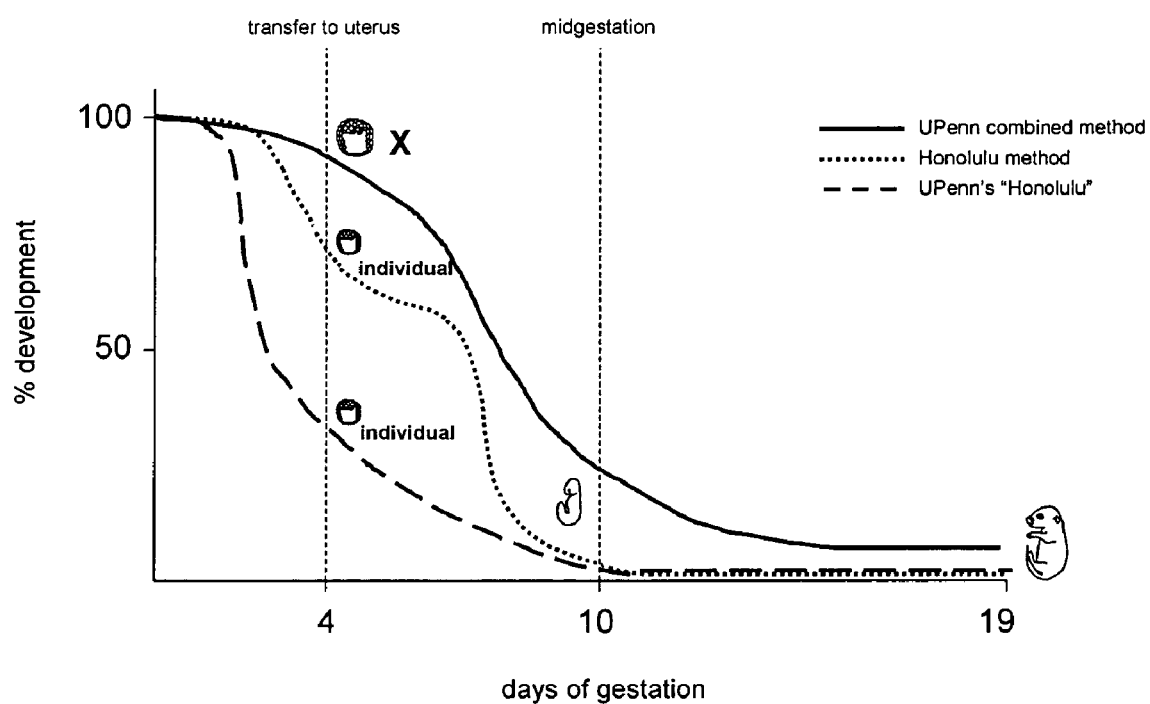
FIG. 3 is a graph depicting the percentage of embryos to develop from formation through blastocyst formation through the end of gestation. The instant invention (UPenn method; wherein the embryos are combined) is compared to the Honolulu method as reported and the Honolulu method as performed by the inventors (UPenn's Honolulu).

For the method of aggregation, a microwell was obtained by gently pressing a darning needle (BLS, Budapest, Hungary) on the bottom of culture dishes in a 3×3 arrangement thereby creating 9 wells. The wells were covered by microdrops of α-MEM, overlaid with oil, and incubated for at least one hour prior to use. Embryos at the 4-cell stage were deprived of the zona pellucida by exposure to acidic Tyrode solution (Sigma). The zona-free embryos were washed thoroughly in α-MEM containing 3% albumin prior to incubation in regular α-MEM. Single clone (1X), double clone (2X), triple clone (3X), and quadruple clone (4X) aggregates were cultured in parallel in the same dish (FIGS. 2 and 5; data not shown). This method has produced up to 100% blastocyst formation (FIG. 3). Table 2 characterizes the produced blastocysts. Importantly, the Oct4 expression pattern of the aggregates more closely resembled the normal pattern of fertilized embryos than the 1X clones.

TABLE 2

| Clone | 4-cell n | Aggregates n | Blastocysts n (% of aggregates) | Total cells mean ± SEM | ICM cells I.S.H. | Replicates n |
|---|---|---|---|---|---|---|
| 1X | 262 | 262 | 65 (25) | 42 ± 2.3 | 17 | 15 |
| 2X | 786 | 393 | 171 (44) | 50 ± 1.7 | 23 | 17 |
| 3X | 504 | 168 | 91 (54) | 62 ± 2.8 | 31 | 10 |

| | Oct4 signal - n embryos (%) | | | |
|---|---|---|---|---|
| Clone | ICM | ICM + TE | absent | Replicates |
| 1X | 13 (37)[a] | 13 (37) | 9 (26) | 2 |
| 2X | 8 (57)[a,c] | 4 (29) | 2 (14) | 2 |
| 3X | 12 (67)[b,c] | 3 (17) | 3 (17) | 2 |
| Fertilized | 21 (78)[b] | 0 (0) | 6 (22) | 3 |

I.S.H., in situ hybridization for Oct4 mRNA;
Different superscript letters within a column are significantly different ($P < 0.05$).

The outgrowth and embryonic stem cell forming capabilities of the aggregate clones were tested as follows. Zona-free single and aggregate clones were plated on a confluent feeder layer of mitomycin C-inactivated STO neo LIF cells (SNL; mouse embryonic fibroblasts derived from the SIM strain and transformed with a neomycin resistance gene and a LIF transgene) in a 4-well plate. Feeder cells and embryos (outgrowths) were cultured in DMEM (supplemented with 4.5 g/L glucose, 0.1 mM non-essential amino acids, 2 mM L-glutamine, 0.5 mM β-mercaptoethanol, 14% FBS, 50 U/ml penicillin/streptomycin). Outgrowth formation was defined by the spreading of trophoblast cells from the attached blastocyst. To determine embryonic stem cell forming ability, outgrowths were disaggregated by trypsinization and grown on feeder layers for 6 days. Subsequent passaging of ES colonies was performed as described (Abbondanzo et al. (1993) Methods Enzymol. 225:803-823). Results from a representative experiment are shown in Table 3. Notably, even blastocysts without an inner cell mass (ICM) can attach and form an outgrowth when the zona pellicuda is removed thereby leading to a high number of 1X outgrowth formations. Indeed, the outgrowths from the 1X clones were frequently small, lacked an Oct4-GFP expressing cell mass, and were poor sources of ES cells. In contrast, aggregate clones were larger, expressed the Oct4-GFP transgene, and were more efficient sources of ES cells.

TABLE 3

| Clone | Blastocysts Plated (n) | Outgrowths formed n (%) | GFP-positive outgrowths n (%) | ES cell lines derived p #1 | Replicates n |
|---|---|---|---|---|---|
| 1X | 38 | 28 (74) | 10 (36)[a] | 2 | 8 |
| 2X | 73 | 62 (85) | 47 (76)[b] | 10 | 8 |
| 3X | 26 | 23 (88) | 19 (83)[b] | n.d. | n.d. |

Different superscript letters within a column are significantly different ($P < 0.05$).

Figure 4:
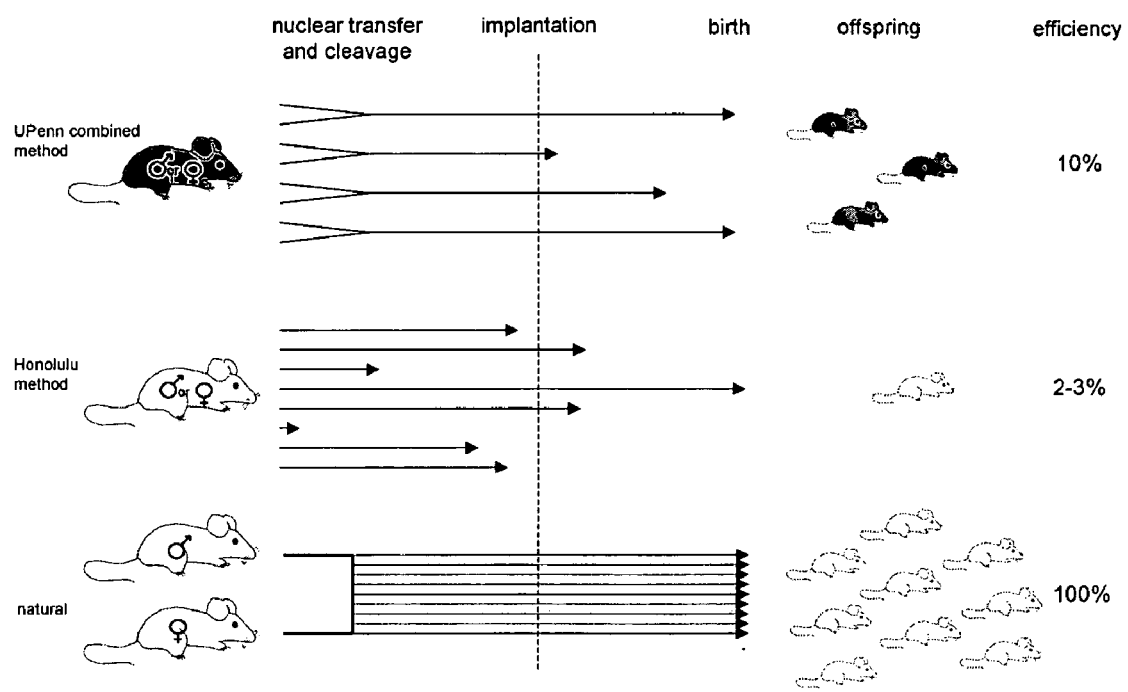
FIG. 4 is a schematic drawing comparing the cloning methods of the instant invention with the Honolulu method and natural reproduction.

The in vivo potential of aggregates was tested by introducing the blastocysts into recipient female mice. Two and four cell stage clone embryos which have not yet begun to express Oct-4, are typically transferred into the oviducts of 4-6 week old pseudopregnant mice that had been mated with vasectomized males on the day of the copulation plug (0.5 days post coitum, d.p.c.). Blastocyst stage clones are, however, transferred into the uterus horns of pseudopregnant females 2.5 d.p.c. Recipient females that had been plugged by vasectomized males were anesthetized using a mixture of xylazine (e.g. Rompun®) and ketamine (e.g. Ketalar®) at 0.2 mg and 0.3 mg per 10 g of body weight, respectively. Prior to transfer, embryos were rinsed in Hepes-buffered CZB medium containing polyvynilpyrrolidone. The tip of a mouth-operated micropipette carrying the embryos was inserted through a hole made in the uterus wall by a 27 gauge needle. In contrast to previously employed methods of clone embryo transfer in which only one offspring was obtained, double, triple, and quadruple pups were typically obtained from a single gestation with the instant method (FIG. 6). Additionally, greater than 10% of 4-cell aggregations were capable of postimplantation development and birth in contrast to less than 5% with previously employed methods (FIGS. 3 and 4).

The results of a representative trial are provided in Table 4. The implantation rates for both single and aggregate zona free blastocysts was substantially higher than observed for clones with intact zona. However, the fetal development in single clones was similar to that of zona intact clones indicating that the higher implantation rate was due to zona removal. In contrast, aggregation resulted in improved development to midgestation (10.5 d.p.c.) with 2X blastocysts yielding more fetuses than single clones. Aggregation also resulted in an increase in biomass, e.g., the size of the deciduas (30% larger, on average).

TABLE 4

| Clone | Blastocysts Transferred (n) | Pregnancies/ recipients (n) | Deciduan (%) | Fetuses 10.5 d.p.c. n (% of blastocysts) |
|---|---|---|---|---|
| 1X | 26 | 4/4 | 17 (65) | 1 (3.8)$^a$ |
| 2X | 43 | 4/4 | 36 (83) | 11 (25.6)$^b$ |

Different superscript letters within a column are significantly different (P < 0.05).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for preparing a non-primate mammalian blastocyst capable of developing into a live-born animal, comprising:
   a) providing genetically identical reconstructed non-primate mammalian embryos;
   b) removing the zona pellucida of said reconstructed embryos;
   c) forming a homologous aggregate of at least two of the zona-free embryos of step b); and
   d) culturing the homologous embryo aggregate of c) under conditions which result in the formation of a non-primate mammalian blastocyst;
   wherein said reconstructed embryos are prepared from reconstructed non-primate mammalian oocytes comprising donor cell nuclei or donor nuclear DNA; wherein said donor cell is a non-primate mammalian embryonic stem cell or a non-primate mammalian embryonic germ cell; and wherein said at least two zona-free embryos in step c) are at the four-cell stage.

2. The method of claim 1, wherein said reconstructed oocytes are prepared by fusion of donor cells to said enucleated oocytes.

3. The method of claim 1, wherein said reconstructed oocytes are prepared via injection of donor nuclei or donor nuclear DNA.

4. The method of claim 1, further comprising implanting said blastocyst into a recipient female so as to produce a fetus that undergoes full fetal development and parturition to generate said live born animal.

5. The method of claim 1, wherein said reconstructed embryo is formed from a reconstructed oocyte which comprises a donor cell nucleus transformed with a heterologous nucleic acid sequence or nuclear DNA isolated from said nucleus prior to transferring said nucleus into an enucleated oocyte.

6. The method of claim 5, wherein the oocyte is enucleated by incubating the oocyte with a spindle disrupting agent and removing the chromosomes by micromanipulation.

7. The method of claim 1, wherein the zona pellucida is removed in step b) by exposing the embryos to acidic Tyrode solution.

8. The method of claim 1, wherein the zona-free embryos have not yet begun to express Oct-4.

9. The method of claim 1, wherein the homologous aggregate formed in step c) comprises genetically identical embryos which are not epigenetically identical.

10. The method of claim 1, wherein the homologous aggregate formed in step c) comprises embryos derived from different cell types of the same animal.

11. A method for preparing a non-primate blastocyst capable of developing into a live-born animal, comprising:
   a) providing genetically identical reconstructed embryos;
   b) removing the zona pellucida of said reconstructed embryos;
   c) forming a homologous aggregate of at least two of the zona-free embryos of step b); and
   d) culturing the homologous embryo aggregate of c) under conditions which result in the formation of a blastocyst;
   wherein said reconstructed embryos are prepared from reconstructed oocytes comprising donor cell nuclei or donor nuclear DNA;
   wherein said reconstructed embryo is from an animal selected from the group consisting of ovine, bovine, equine, goat, feline, canine, rabbit, murine, and porcine; and
   wherein said at least two zona-free embryos in step c) are at the four-cell stage.

12. The method of claim 11, wherein said donor cell is a somatic cell.

13. The method of claim 11, wherein said donor cell is an embryonic stem cell.

14. The method of claim 11, wherein said donor cell is an embryonic germ cell.

15. The method of claim 11, wherein said reconstructed oocytes are prepared by fusion of donor cells to said enucleated oocytes.

16. The method of claim 11, wherein said reconstructed oocytes are prepared via injection of donor nuclei or donor nuclear DNA.

17. The method of claim 11, further comprising implanting said blastocyst into a recipient female so as to produce a fetus that undergoes full fetal development and parturition to generate said live born animal.

18. The method of claim 11, wherein said reconstructed embryo is formed from a reconstructed oocyte which comprises a donor cell nucleus transformed with a heterologous nucleic acid sequence or nuclear DNA isolated from said nucleus prior to transferring said nucleus into an enucleated oocyte.

19. The method of claim 11, wherein the oocyte is enucleated by incubating the oocyte with a spindle disrupting agent and removing the chromosomes by micromanipulation.

20. The method of claim 11, wherein the zona pellucida is removed in step b) by exposing the embryos to acidic Tyrode solution.

21. The method of claim 11, wherein the zona-free embryos have not yet begun to express Oct-4.

22. The method of claim 11, wherein the homologous aggregate formed in step c) comprises genetically identical embryos which are not epigenetically identical.

23. The method of claim 11, wherein the homologous aggregate formed in step c) comprises embryos derived from different cell types of the same animal.

24. A homologous, isolated non-primate mammalian embryo aggregate having increased biomass and excess extranuclear cytoplasmic factors which facilitate gene expression and blastocyst formation and enhance viability of said embryo, wherein said embryo aggregate lacks a zona pellucida, wherein said embryo aggregate comprises at least two genetically identical reconstructed non-primate mammalian embryos, and wherein said embryos are at the four-cell stage.

25. The embryo aggregate of claim 24, of an origin selected from the group consisting of murine, bovine, equine, canine, and feline.

26. The embryo aggregate of claim 24 which comprises genetically identical embryos which are not epigenetically identical.

27. The embryo aggregate of claim 24, which comprises embryos derived from different cell types of the same animal.

28. The embryo aggregate of claim 24, wherein the embryo aggregate is non-human.

* * * * *